United States Patent
Lipkens et al.

(10) Patent No.: US 9,783,775 B2
(45) Date of Patent: *Oct. 10, 2017

(54) BIOREACTOR USING ACOUSTIC STANDING WAVES

(71) Applicant: FloDesign Sonics, Inc., Wilbraham, MA (US)

(72) Inventors: Bart Lipkens, Hampden, MA (US); Louis Masi, Longmeadow, MA (US); Stanley Kowalski, III, Wilbraham, MA (US); Walter M. Presz, Jr., Wilbraham, MA (US); Jason Dionne, Simsbury, CT (US); Brian Dutra, Windsor Locks, CT (US); Ari Mercado, Agawam, MA (US); Thomas J. Kennedy, III, Wilbraham, MA (US); Arthur Martin, Sutton, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/432,737

(22) Filed: Feb. 14, 2017

(65) Prior Publication Data
US 2017/0159005 A1    Jun. 8, 2017

Related U.S. Application Data

(63) Continuation-in-part of application No. 15/238,624, filed on Aug. 16, 2016, now Pat. No. 9,567,559, (Continued)

(51) Int. Cl.
*B01D 17/04* (2006.01)
*C12M 1/00* (2006.01)
*C12M 1/26* (2006.01)

(52) U.S. Cl.
CPC ............ *C12M 47/02* (2013.01); *C12M 29/10* (2013.01); *C12M 29/18* (2013.01); *C12M 33/14* (2013.01); *C12M 47/10* (2013.01)

(58) Field of Classification Search
CPC ...... C12M 47/02; C12M 29/18; C12M 23/22; C12M 29/10; C12M 33/08; C12M 35/04; (Continued)

(56) References Cited

U.S. PATENT DOCUMENTS

| 2,473,971 A | 6/1949 | Ross |
| 2,667,944 A | 2/1954 | Crites |

(Continued)

FOREIGN PATENT DOCUMENTS

| DE | 30 27 433 A1 | 2/1982 |
| DE | 32 18 488 A1 | 11/1983 |

(Continued)

OTHER PUBLICATIONS

Alvarez et al.; Shock Waves, vol. 17, No. 6, pp. 441-447, 2008.
(Continued)

*Primary Examiner* — Walter D Griffin
*Assistant Examiner* — Cameron Allen
(74) *Attorney, Agent, or Firm* — Rick Klein, Esq.; Fay Sharpe, LLP

(57) ABSTRACT

A perfusion bioreactor includes at least one ultrasonic transducer that can acoustically generate a multi-dimensional standing wave. The standing wave can be used to retain cells in the bioreactor, and can also be utilized to dewater or further harvest product from the waste materials produced in a bioreactor.

19 Claims, 13 Drawing Sheets

Related U.S. Application Data which is a continuation-in-part of application No. 14/175,766, filed on Feb. 7, 2014, now Pat. No. 9,416,344, which is a continuation-in-part of application No. 14/026,413, filed on Sep. 13, 2013, now Pat. No. 9,458,450, said application No. 14/026,413 is a continuation-in-part of application No. 13/844,754, filed on Mar. 15, 2013.

(60) Provisional application No. 61/761,717, filed on Feb. 7, 2013, provisional application No. 61/611,159, filed on Mar. 15, 2012, provisional application No. 61/611,240, filed on Mar. 15, 2012, provisional application No. 61/708,641, filed on Oct. 2, 2012, provisional application No. 61/754,792, filed on Jan. 21, 2013.

(58) Field of Classification Search
CPC ...... C12N 13/00; B01D 17/04; B01D 21/283; B01D 17/06; B06B 1/0644; H01L 41/0973
See application file for complete search history.

(56) References Cited

U.S. PATENT DOCUMENTS

| | | |
|---|---|---|
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Shwartzman et al. |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,254,661 A | 3/1981 | Kossoff et al. |
| 4,320,659 A | 3/1982 | Lynnworth et al. |
| 4,344,448 A | 8/1982 | Potts |
| 4,398,325 A | 8/1983 | Piaget et al. |
| 4,552,669 A | 11/1985 | Sekellick |
| 4,666,595 A | 5/1987 | Graham |
| 4,673,512 A | 6/1987 | Schram |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Ju-Zhen |
| 4,821,838 A | 4/1989 | Chen |
| 4,836,684 A | 6/1989 | Javorik et al. |
| 4,860,993 A | 8/1989 | Goode |
| 4,878,210 A | 10/1989 | Mitome |
| 4,983,189 A | 1/1991 | Peterson et al. |
| 5,059,811 A | 10/1991 | King et al. |
| 5,062,965 A | 11/1991 | Bernou et al. |
| 5,085,783 A | 2/1992 | Feke et al. |
| 5,164,094 A | 11/1992 | Stuckart |
| 5,225,089 A | 7/1993 | Benes et al. |
| 5,371,729 A | 12/1994 | Yamamoto et al. |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,475,486 A | 12/1995 | Paoli |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,947,299 A | 9/1999 | Vazquez et al. |
| 5,951,456 A | 9/1999 | Scott |
| 6,090,295 A | 7/2000 | Raghavarao et al. |
| 6,166,231 A | 12/2000 | Hoeksema |
| 6,205,848 B1 | 3/2001 | Faber et al. |
| 6,216,538 B1 | 4/2001 | Yasuda et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,475,151 B2 | 11/2002 | Koger et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,641,708 B1 | 11/2003 | Becker et al. |
| 6,649,069 B2 | 11/2003 | DeAngelis |
| 6,699,711 B1 | 3/2004 | Hahn et al. |
| 6,727,451 B1 | 4/2004 | Fuhr et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,075,786 B2 | 12/2011 | Bagajewicz |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 * | 8/2016 | Lipkens ............... B06B 1/0644 |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |

(56) References Cited

U.S. PATENT DOCUMENTS

| | | |
|---|---|---|
| 9,517,474 B2 | 12/2016 | Mao et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181828 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0045107 A1 | 2/2009 | Ward et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0227042 A1 | 9/2009 | Gauer et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn, Jr. et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Wienand et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Rietman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2014/0011240 A1 | 1/2014 | Lipkens et al. |
| 2014/0017758 A1 | 1/2014 | Kniep et al. |
| 2014/0102947 A1 | 4/2014 | Baym et al. |
| 2014/0141413 A1 | 5/2014 | Laugham, Jr. et al. |
| 2014/0319077 A1 | 10/2014 | Lipkens et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0321129 A1 | 11/2015 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Gilmanshin et al. |

FOREIGN PATENT DOCUMENTS

| | | |
|---|---|---|
| DE | 196 48 519 A1 | 6/1998 |
| DE | 103 19 467 B3 | 7/2004 |
| DE | 10 2008 006 501 A1 | 9/2008 |
| EP | 0 292 470 B1 | 11/1988 |
| EP | 0 641 606 | 3/1995 |
| EP | 1 175 931 A1 | 1/2002 |
| EP | 1 254 669 B1 | 11/2002 |
| GB | 2 420 510 A | 5/2006 |
| JP | 9-136090 | 5/1997 |
| RU | 2085933 | 7/1997 |
| SU | 629496 | 10/1978 |
| WO | WO 87/07178 A1 | 12/1987 |
| WO | WO 89/11899 A1 | 12/1989 |
| WO | WO 90/05008 | 3/1990 |
| WO | WO 97/34643 | 9/1997 |
| WO | WO 98/17373 | 4/1998 |
| WO | WO 98/50133 A1 | 11/1998 |
| WO | WO 02/072234 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |

(56) References Cited

FOREIGN PATENT DOCUMENTS

| | | |
|---|---|---|
| WO | WO 2011/023949 A2 | 3/2011 |
| WO | WO 2011/025890 A1 | 3/2011 |
| WO | WO 2011/027146 A2 | 3/2011 |
| WO | WO 2011/131947 A2 | 10/2011 |
| WO | WO 2011/161463 A2 | 12/2011 |
| WO | WO 2013/043297 A1 | 3/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | WO 2014/055219 A2 | 4/2014 |
| WO | WO 2014/124306 A1 | 8/2014 |
| WO | WO 2014/153651 | 10/2014 |
| WO | WO 2015/006730 | 1/2015 |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.

Castilho et al.; Animal Cell Technology: From Biopharmaceuticals to Gene Therapy; 11—Animal Cell Separation; 2008.

Castro; Tunable gap and quantum quench dynamics in bilayer graphene; Jul. 13, 2010; Mathematica Summer School.

Cravotto et al.; Ultrasonics Sonochemistry, vol. 15, No. 5, pp. 898-902, 2008.

Garcia-Lopez, et al; Enhanced Acoustic Separation of Oil-Water Emulsion in Resonant Cavities. The Open Acoustics Journal. 2008, vol. 1, pp. 66-71.

Hill et al.; Ultrasonic Particle Manipulation; Microfluidic Technologies for Miniaturized Analysis Systems, Jan. 2007, pp. 359-378.

Ilinskii et al.; Acoustic Radiation Force on a Sphere in Tissue; AIP Conference Proceedings; 2012.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Li et al.; Electromechanical behavior of PZT-brass unimorphs; J. Am. Ceram. Soc. vol. 82; No. 7; pp. 1733-1740, 1999.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al.; Separation of bacterial spores from flowering water in macro-scale cavities by ultrasonic standing waves; submitted/uploaded to http://arxiv.org/abs/1006.5467 on Jun. 28, 2010.

Lipkens et al., Macro-scale acoustophoretic separation of lipid particles from red blood cells, The Journal of the Acoustical Society of America, vol. 133, Jun. 2, 2013, p. 045017, XP055162509, New York, NY.

Meribout et a.; An Industrial-Prototype Acoustic Array for Real-Time Emulsion Layer Detection in Oil Storage Tanks; IEEE Sensors Journal, vol. 9, No. 12, Dec. 2009.

Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).

Ponomarenko et al.; Density of states and zero Landau level probed through capacitance of graphene; Nature Nanotechnology Letters, Jul. 5, 2009; DOI: 10.1038/NNANO.2009.177.

Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.

Seymour et al, J. Chem. Edu., 1990, 67(9), p. 763, published Sep. 1990.

Volpin et al.; Mesh simplification with smooth surface reconstruction; Computer-Aided Design; vol. 30; No. 11; 1998.

Wang et al.; Retention and Viability Characteristics of Mammalian Cells in an Acoustically Driven Polymer Mesh; Biotechnol. Prog. 2004, pp. 384-387 (2004).

Wicklund et al.; Ultrasonic Manipulation of Single Cells; Methods in Molecular Biology; vol. 853; pp. 1777-196; 2012.

Annex to Form PCT/ISA/206—Communication Relating to the Results of the Partial International Search Report, dated Jul. 18, 2013.

European Search Report of European Application No. 11769474.5, dated Sep. 5, 2013.

European Search Report of European Application No. 13760840.2, dated Feb. 4, 2016.

European Search Report of European Application No. 13721179.3 dated Feb. 23, 2016.

International Search Report and Written Opinion dated Dec. 20, 2011, for corresponding PCT application No. PCT/US2011/032181.

International Search Report and Written Opinion dated Feb. 27, 2012, for PCT application No. PCT/US2011/040787.

International Search Report and Written Opinion of International Application No. PCT/US2012/051804 dated Nov. 16, 2012.

International Search Report and Written Opinion of International Application No. PCT/US2013/037404 dated Jun. 21, 2013.

International Search Report and Written Opinion of International Application No. PCT/US2013/032705 dated Jul. 26, 2013.

International Search Report and Written Opinion of International Application No. PCT/US2013/050729 dated Sep. 25, 2013.

International Search Report dated Feb. 18, 2014 in corresponding PCT Application No. PCT/US2013/059640.

International Search Report for corresponding PCT Application Serial No. PCT/US2014/015382 dated May 6, 2014.

International Search Report for PCT/US2014/035557 dated Aug. 27, 2014.

International Search Report for PCT/US2014/043930 dated Oct. 22, 2014.

International Search Report for PCT/US2014/046412 dated Oct. 27, 2014.

International Search Report for PCT/US2014/064088 dated Jan. 30, 2015.

Extended European Search Report for Application No. EP 12833859.7 dated Mar. 20, 2015.

International Search Report and Written Opinion for International Application No. PCT/US2015/010595 dated Apr. 15, 2015.

International Search Report for PCT/US2015/019755 dated May 4, 2015.

International Search Report mailed Jul. 30, 2015 for International Application No. PCT/US2015/030009.

International Search Report for PCT/US2015/039125 dated Sep. 30, 2015.

International Search Report and Written Opinion for PCT Application Serial No. PCT/US2015/053200 dated Dec. 28, 2015.

European Search Report of European Application No. 11796470.0 dated Jan. 5, 2016.

International Search Report and Written Opinion for International Application No. PCT/US2015/066884, dated Mar. 22, 2016.

(56) References Cited

OTHER PUBLICATIONS

International Search Report and Written Opinion for International Application No. PCT/US2016/024082 dated Jun. 27, 2016.
International Search Report and Written Opinion for International Application No. PCT/US2016/044586 dated Oct. 21, 2016.
International Search Report and Written Opinion for International Application No. PCT/US2016/031357 dated Jul. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.

* cited by examiner

BIOREACTOR USING ACOUSTIC STANDING WAVES

CROSS-REFERENCE TO RELATED APPLICATIONS

This application is a continuation-in-part of U.S. patent application Ser. No. 15/238,624, filed Aug. 16, 2016, which is a continuation-in-part of U.S. patent application Ser. No. 14/175,766, filed Feb. 7, 2014, which claims the benefit of U.S. Provisional Patent Application Ser. No. 61/761,717, filed on Feb. 7, 2013, and which is also a continuation-in-part of U.S. patent application Ser. No. 14/026,413, filed on Sep. 13, 2013, which is a continuation-in-part of U.S. Ser. No. 13/844,754, filed Mar. 15, 2013, which claimed the benefit of U.S. Provisional Patent Application Ser. No. 61/708,641, filed on Oct. 2, 2012, and of U.S. Provisional Patent Application Ser. No. 61/611,159, filed Mar. 15, 2012, and of U.S. Provisional Patent Application Ser. No. 61/611,240, also filed Mar. 15, 2012, and of U.S. Provisional Patent Application Ser. No. 61/754,792, filed Jan. 21, 2013. These applications are incorporated herein by reference in their entireties.

BACKGROUND

The field of biotechnology has grown tremendously in the last 20 years. This growth has been due to many factors, some of which include the improvements in the equipment available for bioreactors, the increased understanding of biological systems and increased knowledge as to the interactions of materials (such as monoclonal antibodies and recombinant proteins) with the various systems of the human body.

Improvements in equipment have allowed for larger volumes and lower cost for the production of biologically derived materials such as recombinant proteins. This is especially prevalent in the area of pharmaceuticals, where the successes of many types of new drug therapies have been directly due to the ability to mass produce these materials through protein-based manufacturing methods.

One of the key components that is utilized in the manufacturing processes of new biologically based pharmaceuticals is the bioreactor and the ancillary processes associated therewith. An area of growth in the bioreactor field has been with the perfusion process. The perfusion process is distinguished from the fed-batch process by its lower capital cost and higher throughput.

In the fed-batch process, a culture is seeded in a bioreactor. The gradual addition of a fresh volume of selected nutrients during the growth cycle is used to improve productivity and growth. The product is recovered after the culture is harvested. The fed batch bioreactor process has been attractive because of its simplicity and also due to carryover from well-known fermentation processes. However, a fed-batch bioreactor has high start-up costs, and generally has a large volume to obtain a cost-effective amount of product at the end of the growth cycle. After the batch is completed, the bioreactor must be cleaned and sterilized, resulting in nonproductive downtime.

A perfusion bioreactor processes a continuous supply of fresh media that is fed into the bioreactor while growth-inhibiting byproducts are constantly removed. The nonproductive downtime can be reduced or eliminated with a perfusion bioreactor process. The cell densities achieved in perfusion culture (30-100 million cells/mL) are typically higher than for fed-batch modes (5-25 million cells/mL). However, a perfusion bioreactor requires a cell retention device to prevent escape of the culture when byproducts are being removed. These cell retention systems add a level of complexity to the perfusion process, requiring management, control, and maintenance for successful operation. Operational issues such as malfunction or failure of the cell retention equipment has previously been a problem with perfusion bioreactors. This has limited their attractiveness in the past.

BRIEF DESCRIPTION

The present disclosure relates, in various embodiments, to a system for producing biomolecules such as recombinant proteins or monoclonal antibodies, and for separating these desirable products from a cell culture in a bioreactor. Generally, a fluid medium containing the cells and the desired products are passed or flowed through a filtering device. The present disclosure also relates, in various other embodiments, to a system for generating cells. In some embodiments, such generated cells may be for use in a cell therapy process. In such embodiments, the desired cells (e.g., T cells, B cells, or NK cells) are cultured and expanded in a host fluid in a bioreactor. The host fluid is then flowed through a filtering device to capture some of the cells, while the remaining cells continue to be cultured in the bioreactor. In some embodiments, the cells are plant cells used for bio-agriculture techniques, for example in the production of phytochemicals or insect resistant plants.

Disclosed in various embodiments is a system comprising a bioreactor and a filtering device. The bioreactor includes a reaction vessel, an agitator, a feed inlet, and an outlet. The filtering device comprises: an inlet fluidly connected to the bioreactor outlet for receiving fluid from the bioreactor; a flow chamber through which the fluid can flow; and at least one ultrasonic transducer and a reflector located opposite the at least one ultrasonic transducer, the at least one ultrasonic transducer being driven to produce a multi-dimensional standing wave in the flow chamber.

The filtering or trapping device for the bioreactor may also consist of a flow chamber with one or more ultrasonic transducers and reflectors incorporated into the flow chamber. The reflectors are set up opposite the ultrasonic transducers and the ultrasonic transducers are electronically driven to form a multi-dimensional acoustic standing wave in the flow chamber.

The flow chamber may be made from a rigid material, such as a plastic, glass or metal container. The flow chamber may alternatively be in the form of a flexible polymeric bag or pouch that is capable of being sealed and removed from the recirculation path between the bioreactor outlet through the external filtering device and a recycle inlet of the bioreactor. This flexible polymeric bag or pouch may be located between an ultrasonic transducer and a reflector such that a multi-dimensional acoustic standing wave may be generated interior to the flexible polymeric bag or pouch.

The filtering device may further comprise a product outlet through which desired product, such as expanded cells, viruses, exosomes, or phytochemicals are recovered. The filtering device can also further comprise a recycle outlet for sending fluid back to the bioreactor.

The multi-dimensional standing wave may have an axial force component and a lateral force component which are of the same order of magnitude. The bioreactor can be operated as a perfusion bioreactor.

The sleeve may be separable from the flow chamber. Sometimes, the filtering device further comprises a jacket located between the sleeve and the flow chamber, the jacket being used to regulate the temperature of the fluid in the flow chamber. The jacket, the sleeve, and the flow chamber can be separable from each other and be disposable.

In particular embodiments, the ultrasonic transducer comprises a piezoelectric material that can vibrate in a higher order mode shape. The piezoelectric material may have a rectangular shape.

The ultrasonic transducer may comprise: a housing having a top end, a bottom end, and an interior volume; and a crystal at the bottom end of the housing having an exposed exterior surface and an interior surface, the crystal being able to vibrate when driven by a voltage signal. In some embodiments, a backing layer contacts the interior surface of the crystal, the backing layer being made of a substantially acoustically transparent material. The substantially acoustically transparent material can be balsa wood, cork, or foam. The substantially acoustically transparent material may have a thickness of up to 1 inch. The substantially acoustically transparent material can be in the form of a lattice. In other embodiments, an exterior surface of the crystal is covered by a wear surface material with a thickness of a half wavelength or less, the wear surface material being a urethane, epoxy, or silicone coating. In yet other embodiments, the crystal has no backing layer or wear layer.

The ultrasonic transducer may also comprise a piezoelectric material that is polymeric such as polyvinylidene fluoride (PVDF). The PVDF may be excited at higher frequencies up to the hundreds of megahertz range such that very small particles may be trapped by the acoustic standing wave.

The multi-dimensional standing wave can be a three-dimensional standing wave.

The reflector may have a non-planar surface.

The product outlet of the filtering device may lead to a further process such as cell washing, cell concentration or cell fractionation. Such processes may be applied when the recovered product is biological cells such as T cells, B cells and NK cells. In certain embodiments, the cells used to produce viruses or exosomes are Chinese hamster ovary (CHO) cells, NS0 hybridoma cells, baby hamster kidney (BHK) cells, or human cells. The use of mammalian cell cultures including the aforementioned cell types has proven to be a very efficacious way of producing/expressing the recombinant proteins and monoclonal antibodies required of today's pharmaceuticals. In some embodiments, the cells are plant cells that produce secondary metabolites and recombinant proteins and other phytochemicals.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
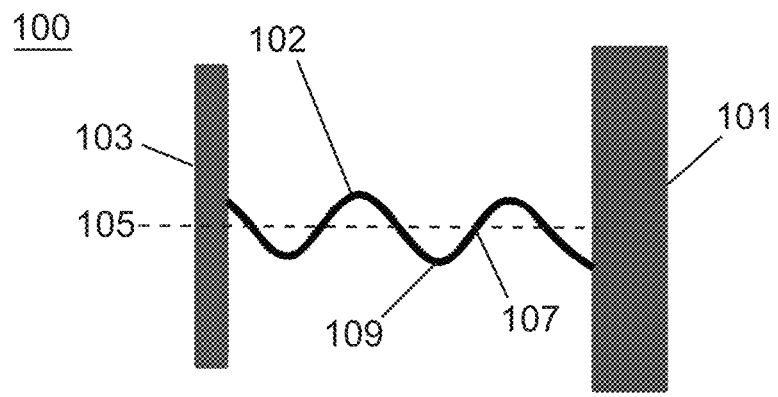
FIG. 1 illustrates a single standing acoustic wave generated by an ultrasonic transducer and a reflector.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10."

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The present application refers to "the same order of magnitude." Two numbers are of the same order of magnitude if the quotient of the larger number divided by the smaller number is a value of at least 1 and less than 10.

The term "virus" refers to an infectious agent that can only replicate inside another living cell, and otherwise exists in the form of a virion formed from a capsid that surrounds and contains DNA or RNA, and in some cases a lipid envelope surrounding the capsid.

The term "exosome" refers to a vesicle, which has a lipid bilayer surrounding a core of fluid that contains proteins, DNA, and/or RNA.

The term "crystal" refers to a single crystal or polycrystalline material that is used as a piezoelectric material.

Bioreactors are useful for making biomolecules such as recombinant proteins or monoclonal antibodies. Very generally, cells are cultured in a bioreactor vessel with media in order to produce the desired product, and the desired product is then harvested by separation from the cells and media. The use of mammalian cell cultures including Chinese hamster ovary (CHO), NS0 hybridoma cells, baby hamster kidney (BHK) cells, and human cells has proven to be a very efficacious way of producing/expressing the recombinant proteins and monoclonal antibodies used in pharmaceuticals. Two general types of bioreactor processes exist: fed-batch and perfusion.

While fed-batch reactors are the norm currently, due mainly to the familiarity of the process to many scientists and technicians, perfusion technology is growing at a very fast clip. Many factors favor the use of a perfusion bioreactor process. The capital and start-up costs for perfusion bioreactors are lower, smaller upstream and downstream capacity is required, and the process uses smaller volumes and fewer seed steps than fed-batch methods. A perfusion bioreactor process also lends itself better to development, scale-up, optimization, parameter sensitivity studies, and validation.

Recent developments in perfusion bioreactor technology also favor its use. Control technology and general support equipment is improving for perfusion bioreactors, increasing the robustness of perfusion processes. The perfusion process can now be scaled up to bioreactors having a volume up to 1000 liters (L). Better cell retention systems for perfusion bioreactors result in lower cell loss and greater cell densities than have been seen previously. Cell densities greater than 50 million cells/mL are now achievable, compared to fed-batch cell densities of around 20 million cells/mL. Lower contamination and infection rates have improved the output of perfusion bioreactors. Higher product concentrations in the harvest and better yields without significant increase in cost have thus resulted for perfusion processes.

A separate aspect of the use of high cell concentration bioreactors is the "dewatering" of the materials at the end of a bioreactor run. The "dewatering" or removal of interstitial fluid from a bioreactor sludge is important for improving the efficiency of recovery of the intended bioreactor product. Currently, high energy centrifuges with internal structures (known as disk stack centrifuges) are utilized to remove the interstitial fluid from the bioreactor sludge at the end of a run. The capital cost and operating costs for a disk stack centrifuge is high. A simpler method of removing the interstitial fluid from the remaining bioreactor sludge that can be performed without the high capital and operating costs associated with disk stack centrifuges is desirable. In addition, current methods of filtration or centrifugation can damage cells, releasing protein debris and enzymes into the purification process and increasing the load on downstream portions of the purification system.

Briefly, the present disclosure relates to the generation of multi-dimensional (e.g., three-dimensional (3-D)) acoustic standing wave(s) from one or more piezoelectric transducers, where the transducers are electrically or mechanically excited such that they move in a "drumhead" or multi-excitation mode (i.e., multi-mode displacement pattern), rather than a "piston" or single excitation mode fashion. Through this manner of acoustic standing wave generation, a higher lateral trapping force is generated than if the piezoelectric transducer is excited in a "piston" mode where only one large standing wave is generated. Thus, with the same input power to a piezoelectric transducer, the multi-dimensional (e.g., 3-D) acoustic standing wave(s) can have a higher lateral trapping force compared to a single planar acoustic standing wave. The input power is tunable for a controlled flow. This can be used to facilitate proteinaceous fluid purification of the contents of a bioreactor. Thus, the present disclosure relates to processing systems comprising a bioreactor and a filtering device, the filtering device using acoustophoresis for separation of various components.

Through utilization of an acoustophoretic filtering device that incorporates a multi-dimensional (e.g., 3-D) standing wave, maintaining flux rates and minimizing cross-contamination risk in a multiproduct system can also be achieved. Other benefits, such as cleaning procedures and related demands often detailed and validated within standard operating procedures (SOP), can also be realized through the use of a multi-dimensional (e.g., 3-D) acoustic standing wave capable apparatus. The cross-contamination risk can be eliminated between the bioreactor and outside processes.

Acoustophoresis is a low-power, no-pressure-drop, no-clog, solid-state approach to particle removal from fluid dispersions: i.e., it is used to achieve separations that are more typically performed with porous filters, but it has none of the disadvantages of filters. In particular, the present disclosure provides filtering devices that are suitable for use with bioreactors and operate at the macro-scale for separations in flowing systems with high flow rates. The acoustophoretic filtering device is designed to create a high intensity multi-dimensional (e.g., three dimensional) ultrasonic standing wave that results in an acoustic radiation force that is larger than and can overcome the combined effects of fluid drag and buoyancy or gravity at certain flow rates, and is therefore able to trap (i.e., hold stationary) the suspended phase (i.e. cells) to allow more time for the acoustic wave to increase particle concentration, agglomeration and/or coalescence. Put another way, the radiation force of the acoustic standing wave(s) acts as a filter that prevents or retards targeted particles (e.g., biological cells) from crossing through the standing wave(s). The present systems have the ability to create ultrasonic standing wave fields that can trap particles in flow fields with a linear velocity ranging from 0.1 mm/sec to velocities exceeding 1 cm/s. As explained above, the trapping capability of a standing wave may be varied as desired, for example by varying the flow rate of the fluid, the acoustic radiation force, and the shape of the acoustic filtering device to maximize cell retention through trapping and settling. This technology offers a green and sustainable alternative for separation of secondary phases with a significant reduction in cost of energy. Excellent particle separation efficiencies have been demonstrated for particle sizes as small as one micron.

The ultrasonic standing waves can be used to trap, i.e., hold stationary, secondary phase particles (e.g. cells) in a host fluid stream (e.g. cell culture media). This is an important distinction from previous approaches where particle trajectories were merely altered by the effect of the acoustic radiation force. The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable positions within the standing waves. When the acoustic radiation force exerted on the particles is stronger than the combined effect of fluid drag force and buoyancy/gravitational force, the particle is trapped within the acoustic standing wave field. The action of the acoustic forces (i.e., the lateral and axial acoustic forces) on the trapped particles results in formation of tightly-packed clusters through concentration, clustering, clumping, agglomeration and/or coalescence of particles that, when reaching a critical size, settle continuously through enhanced gravity for particles heavier than the host fluid or rise out through enhanced buoyancy for particles lighter than the host fluid. Additionally, secondary inter-particle forces, such as Bjerkness forces, aid in particle agglomeration.

Generally, the 3-D standing wave(s) filtering system is operated at a voltage such that the protein-producing materials, such as Chinese hamster ovary cells (CHO cells), the most common host for the industrial production of recombinant protein therapeutics, are trapped in the ultrasonic standing wave, i.e., remain in a stationary position. Within each nodal plane, the CHO cells are trapped in the minima of the acoustic radiation potential. Most biological cell types present a higher density and lower compressibility than the medium in which they are suspended, so that the acoustic contrast factor between the cells and the medium has a positive value. As a result, the axial acoustic radiation force (ARF) drives the biological cells towards the standing wave pressure nodes. The axial component of the acoustic radiation force drives the cells, with a positive contrast factor, to the pressure nodal planes, whereas cells or other particles with a negative contrast factor are driven to the pressure anti-nodal planes. The radial or lateral component of the acoustic radiation force is the force that traps the cells. The radial or lateral component of the ARF is larger than the combined effect of fluid drag force and gravitational force. For small cells or emulsions the drag force $F_D$ can be expressed as:

$$\vec{F}_D = 4\pi\mu_f R_p (\vec{U}_f - \vec{U}_p) \left[ \frac{1 + \frac{3}{2}\hat{\mu}}{1 + \hat{\mu}} \right],$$

where $U_f$ and $U_p$ are the fluid and cell velocity, $R_p$ is the particle radius, $\mu_f$ and $\mu_p$ are the dynamic viscosity of the fluid and the cells, and $\hat{\mu}=\mu_p/\mu_f$ is the ratio of dynamic viscosities. The buoyancy force $F_B$ is expressed as:

$$F_B = \frac{4}{3}\pi R_p^3 (\rho_f - \rho_p).$$

To determine when a cell is trapped in the ultrasonic standing wave, the force balance on the cell may be assumed to be zero, and therefore an expression for lateral acoustic radiation force $F_{LRF}$ can be found, which is given by:

$$F_{LRF} = F_D + F_B.$$

For a cell of known size and material property, and for a given flow rate, this equation can be used to estimate the magnitude of the lateral acoustic radiation force.

One theoretical model that is used to calculate the acoustic radiation force is based on the formulation developed by Gor'kov. The primary acoustic radiation force $F_A$ is defined as a function of a field potential U, $F_A = -\nabla(U)$, where the field potential U is defined as $$U = V_0 \left[ \frac{\langle p^2 \rangle}{2\rho_f c_f^2} f_1 - \frac{3\rho_f \langle u^2 \rangle}{4} f_2 \right],$$

and $f_1$ and $f_2$ are the monopole and dipole contributions defined by $$f_1 = 1 - \frac{1}{\Lambda \sigma^2}, f_2 = \frac{2(\Lambda - 1)}{2\Lambda + 1},$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o$ is the volume of the cell, and $\langle\rangle$ indicates time averaging over the period of the wave.

Gor'kov's theory is limited to particle sizes that are small with respect to the wavelength of the sound fields in the fluid and the particle, and it also does not take into account the effect of viscosity of the fluid and the particle on the radiation force. Additional theoretical and numerical models have been developed for the calculation of the acoustic radiation force for a particle without any restriction as to particle size relative to wavelength. These models also include the effect of fluid and particle viscosity, and therefore are a more accurate calculation of the acoustic radiation force. The models that were implemented are based on the theoretical work of Yurii Ilinskii and Evgenia Zabolotskaya as described in AIP Conference Proceedings, Vol. 1474-1, pp. 255-258 (2012). Additional in-house models have been developed to calculate acoustic trapping forces for cylindrical shaped objects, such as the "hockey pucks" of trapped particles in the standing wave, which closely resemble a cylinder.

The lateral force component of the total acoustic radiation force (ARF) generated by the ultrasonic transducer(s) of the present disclosure is significant and is sufficient to overcome the fluid drag force at linear velocities of up to 1 cm/s, and to create tightly packed clusters, and is of the same order of magnitude as the axial force component of the total acoustic radiation force. This lateral ARF can thus be used to retain cells in a bioreactor while the bioreactor process continues. This is especially true for a perfusion bioreactor.

The filtering devices of the present disclosure, which use ultrasonic transducers and acoustophoresis, can also improve the dewatering of the leftover material from a bioreactor batch (i.e bioreactor sludge), and thus reduce the use of or eliminate the use of disk stack centrifuges. This use or application of ultrasonic transducers and acoustophoresis simplifies processing and reduces costs.

In a perfusion bioreactor system, it is desirable to be able to filter and separate the cells and cell debris from the expressed materials that are in the fluid stream (i.e. cell culture media). The expressed materials are composed of biomolecules such as recombinant proteins or monoclonal antibodies, and are the desired product to be recovered.

An acoustophoretic filtering device can be used in at least two different ways. First, the standing waves can be used to trap the expressed biomolecules and separate this desired product from the cells, cell debris, and media. The expressed biomolecules can then be diverted and collected for further processing. Alternatively, the standing waves can be used to trap the cells and cell debris present in the cell culture media. The cells and cell debris, having a positive contrast factor, move to the nodes (as opposed to the anti-nodes) of the standing wave. As the cells and cell debris agglomerate at the nodes of the standing wave, there is also a physical scrubbing of the cell culture media that occurs whereby more cells are trapped as they come in contact with the cells that are already held within the standing wave. This generally separates the cells and cellular debris from the cell culture media. When the cells in the standing wave agglomerate to the extent where the mass is no longer able to be held by the acoustic wave, the aggregated cells and cellular debris that have been trapped can fall out of the fluid stream through gravity, and can be collected separately. To aid this gravitational settling of the cells and cell debris, the standing wave may be interrupted to allow all of the cells to fall out of the fluid stream that is being filtered. This process can be useful for dewatering. The expressed biomolecules may have been removed beforehand, or remain in the fluid stream (i.e. cell culture medium).

Desirably, the ultrasonic transducer(s) generate a multi-dimensional (e.g., three-dimensional) standing wave in the fluid that exerts a lateral force on the suspended particles to accompany the axial force so as to increase the particle trapping capabilities of the acoustophoretic filtering device. Typical results published in literature state that the lateral force is two orders of magnitude smaller than the axial force. In contrast, the technology disclosed in this application provides for a lateral force to be of the same order of magnitude as the axial force.

In the present disclosure, a perfusion bioreactor can also be used to generate cells that can subsequently be used for cell therapy. In this type of process, the biological cells to be used in the cell therapy are cultured in the bioreactor and expanded (i.e. to increase the number of cells in the bioreactor through cell reproduction). These cells may be lymphocytes such as T cells (e.g., regulatory T-cells (Tregs), Jurkat T-cells), B cells, or NK cells; their precursors, such as peripheral blood mononuclear cells (PBMCs); and the like. The cell culture media (aka host fluid), containing some cells, is then sent to a filtering device that produces an acoustic standing wave. A portion of the cells are trapped and held in the acoustic standing wave, while the remaining host fluid and other cells in the host fluid are returned to the bioreactor. As the quantity of trapped cells increases, they form larger clusters that will fall out of the acoustic standing wave at a critical size due to gravity forces. The clusters can fall into a product outlet outside a region of the acoustic standing wave, such as below the acoustic standing wave, from which the cells can be recovered for use in cell therapy. Only a small portion of the cells are trapped and removed from the bioreactor via the product outlet, and the remainder continue to reproduce in the bioreactor, allowing for continuous production and recovery of the desired cells.

In another application, acoustic standing waves are used to trap and hold biological cells and to separate viruses (e.g. lentiviruses) or exosomes that are produced by the biological cells. In these embodiments, the biological cells are returned to the bioreactor post-separation to continue production of viruses or exosomes.

In these applications, the acoustic filtering devices of the present disclosure can act as a cell retention device. The acoustic cell retention systems described herein operate over a range of cell recirculation rates, efficiently retain cells over a range of perfusion (or media removal) rates, and can be tuned to fully retain or selectively pass some percentage of cells through fluid flow rate, transducer power or frequency manipulation. Power and flow rates can all be monitored and used as feedback in an automated control system.

The cells of interest may also be held in the flow chamber of the external filtering device through the use of an acoustic standing wave such that other moieties may be introduced in close proximity to and for the purpose of changing the target cells. Such an operation would include the trapping of T cells and the subsequent introduction of modified lentivirus materials with a specific gene splice such that the lentivirus with a specific gene splice will transfect the T cell and generate a chimeric antigen receptor T cell also known as a CAR-T cell.

The acoustic filtering devices of the present disclosure are designed to maintain a high intensity three-dimensional acoustic standing wave. The device is driven by a function generator and amplifier (not shown). The device performance is monitored and controlled by a computer. It may be desirable, at times, due to acoustic streaming, to modulate the frequency or voltage amplitude of the standing wave. This modulation may be done by amplitude modulation and/or by frequency modulation. The duty cycle of the propagation of the standing wave may also be utilized to achieve certain results for trapping of materials. In other words, the acoustic beam may be turned on and shut off at different frequencies to achieve desired results.

FIG. 1 illustrates a single standing wave system 100 that is comprised of a reflector plate 101 and an ultrasonic transducer 103 that is set to resonate so as to form a standing wave 102. Excitation frequencies typically in the range from hundreds of kHz to tens of MHz are applied by the transducer 103. One or more standing waves are created between the transducer 103 and the reflector 101. The standing wave is the sum of two propagating waves that are equal in frequency and intensity and that are traveling in opposite directions, i.e. from the transducer to the reflector and back. The propagating waves destructively interfere with each other and thus generate the standing wave. A dotted line 105 is used to indicate the amplitude. A node is a point where the wave has minimum amplitude, and is indicated with reference numeral 107. An anti-node is a point where the wave has maximum amplitude, and is indicated with reference numeral 109.

Figure 2:
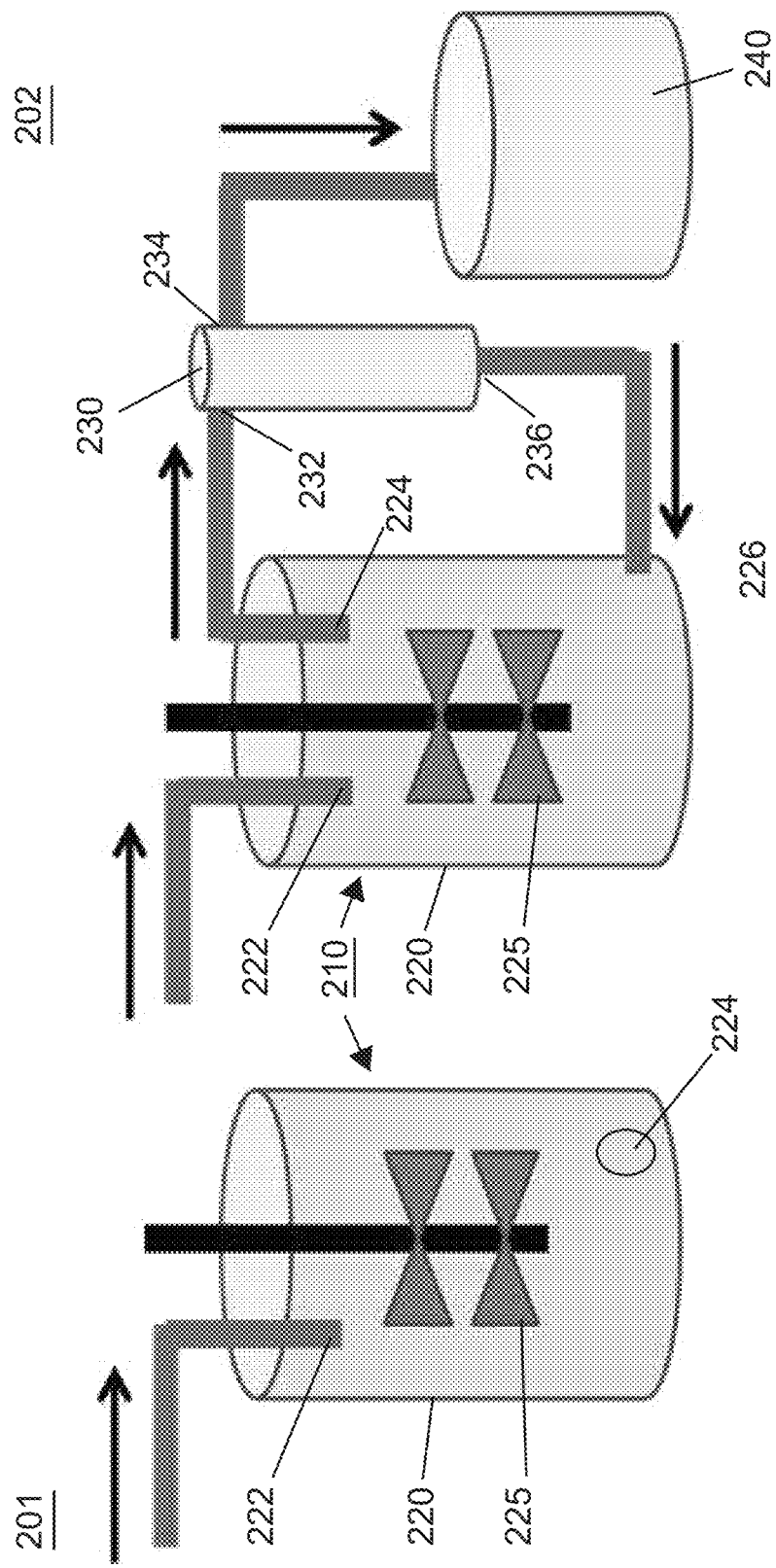
FIG. 2 is an illustration comparing a fed-batch bioreactor system with a perfusion bioreactor system.

FIG. 2 is a schematic diagram that compares a fed-batch bioreactor system 201 (left side) with a perfusion bioreactor system 202 (right side). Beginning with the fed-batch bioreactor on the left, the bioreactor 210 includes a reaction vessel 220. The cell culture media is fed to the reaction vessel through a feed inlet 222. An agitator 225 is used to circulate the media throughout the cell culture. Here, the agitator is depicted as a set of rotating blades, though any type of system that causes circulation is contemplated. The bioreactor permits growth of a seed culture through a growth/production cycle, during which time debris, waste and unusable cells will accumulate in the bioreactor and the desired product (e.g. biomolecules such as monoclonal antibodies, recombinant proteins, hormones, etc.) will be produced as well. Due to this accumulation, the reaction vessel of a fed-batch process is typically much larger than that in a perfusion process. The desired product is then harvested at the end of the production cycle. The reaction vessel 220 also includes an outlet 224 for removing material.

Turning now to the perfusion bioreactor 202 on the right-hand side, again, the bioreactor includes a reaction vessel 220 with a feed inlet 222 for the cell culture media. An agitator 225 is used to circulate the media throughout the cell culture. An outlet 224 of the reaction vessel is fluidly connected to the inlet 232 of a filtering device 230, and continuously feeds the media (containing cells and desired product) to the filtering device. The filtering device 230 is located downstream of the reaction vessel, and separates the desired product from the cells. The filtering device 230 has two separate outlets, a product outlet 234 and a recycle outlet 236. The product outlet 234 fluidly connects the filtering device 230 to a containment vessel 240 downstream of the filtering device, which receives a concentrated flow of the desired product (plus media) from the filtering device. From there, further processing/purification can occur to isolate/recover the desired product. The recycle outlet 236 fluidly connects the filtering device 230 back to a recycle inlet 226 of the reaction vessel 220, and is used to send the cells and cell culture media back into the reaction vessel for continued growth/production. Put another way, there is a fluid loop between the reaction vessel and the filtering device. The reaction vessel 220 in the perfusion bioreactor system 202 has a continuous throughput of product and thus can be made smaller than the fed-batch bioreactor system 201. The filtering process is critical to the throughput of the perfusion bioreactor. A poor filtering process will allow for only low throughput and result in low yields of the desired product.

Figure 3:
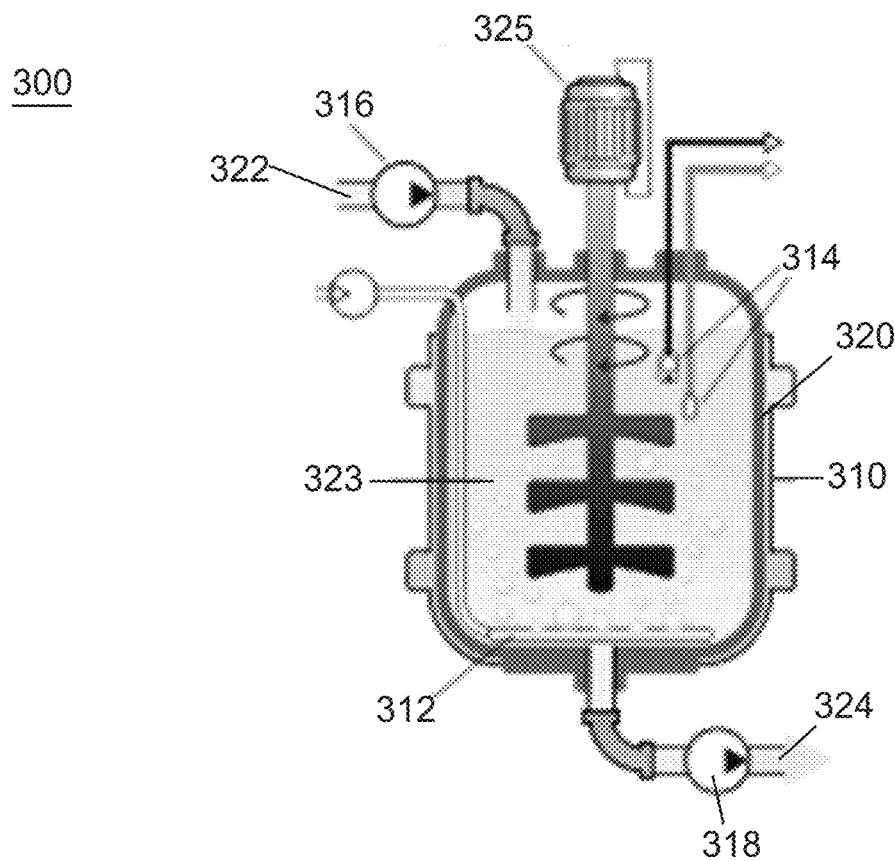
FIG. 3 is a cross-sectional view that shows the various components of a bioreactor.

FIG. 3 is a cross-sectional view of a generic bioreactor 300 that is useful for the systems of the present disclosure. As illustrated here, the bioreactor includes a reaction vessel 320 having an internal volume 323. A feed inlet 322 at the top of the vessel is used to feed cell culture media into the vessel. An agitator 325 is present. An outlet 324 is shown at the bottom of the vessel. A thermal jacket 310 surrounds the reaction vessel, and is used to regulate the temperature of the cells/media. An aerator 312 is located on the bottom of the vessel for providing gas to the internal volume. Sensors 314 are shown at the top right of the vessel. A pump 316 is illustrated for feeding the cell culture media into the vessel, as is another pump 318 for removing cell culture media from the vessel. An interior light source for illuminating the internal volume may be present, for example when the bioreactor is used for growing plant cells.

The perfusion systems of the present disclosure also use an acoustophoretic filtering device. The contents of the bioreactor are continuously flowed through the filtering device to capture the desired products.

Figure 4:
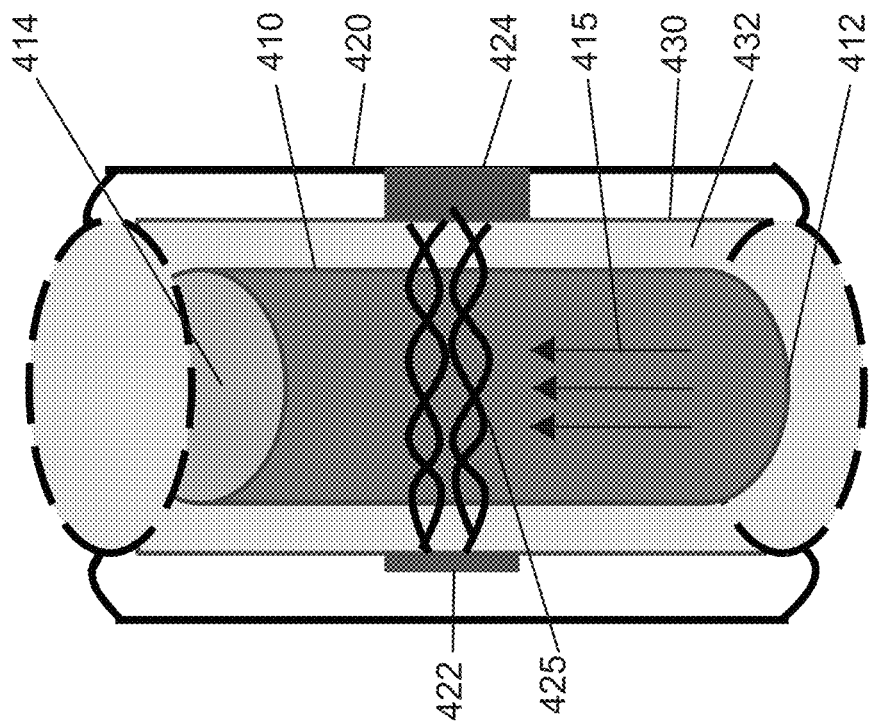
FIG. 4 shows one embodiment of an acoustophoretic filtering device of the present disclosure, with a sleeve surrounding a pipe that acts as a flow chamber and is disposable.

FIG. 4 is a first embodiment of an acoustophoretic filtering device 400. The device includes a flow chamber 410, which is depicted here as a cylindrical pipe or tube. A feed inlet 412 is illustrated here at the bottom of the flow chamber, through which fluid from the bioreactor is received. An outlet 414 is depicted at the top of the flow chamber, with the arrows (reference numeral 415) indicating the direction of fluid flow. A sleeve 420 surrounds the flow chamber. The sleeve includes at least one ultrasonic transducer 422 and at least one reflector 424, which are located opposite each other. Together, the transducer and reflector generate one or more standing waves 425, with the reflector bouncing the initial propagated wave back towards the transducer with a similar frequency and intensity to form an acoustic standing wave. It is particularly contemplated that the sleeve can be separated from the flow chamber/pipe. The pipe can be discarded and replaced with a new pipe. This configuration allows for disposable parts in the filtering device, and thus reduces the cost of cleaning and sterilization that might otherwise be incurred with a permanent filter.

It is noted that the filtering device may include additional inlets or outlets not depicted here, as previously explained.

Figure 5:
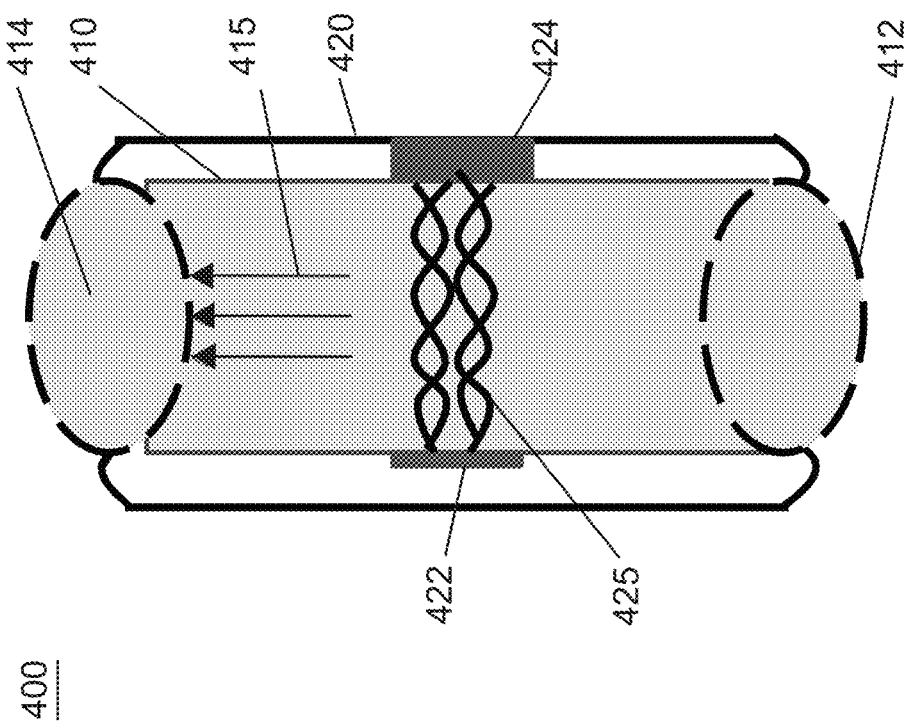
FIG. 5 shows another embodiment of an acoustophoretic filtering device of the present disclosure, showing a jacket surrounding the flow chamber, and the sleeve surrounding the jacket. The sleeve contains a fluid that is used to regulate the temperature of the fluid passing through the flow chamber.

FIG. 5 is a second embodiment of the acoustophoretic filtering device. Here, the filtering device 400 also includes a jacket 430 that is located between the sleeve 420 and the flow chamber 410. The jacket contains a temperature-regulating fluid 432 that can be used to control the temperature of the fluid passing through the flow chamber. In this regard, it is usually desirable to maintain the temperature of the cell culture below 38° C. to prevent compromise of the cells. The temperature-regulating fluid is completely separated from the cell culture media/fluid passing through the flow chamber 410. It is noted that the standing wave 425 created by the transducer 422 and reflector 424 will propagate through the jacket 430 and the temperature regulating fluid 432 therein, and will continue to operate in the flow chamber to separate the targeted material in the flow chamber.

Figure 6:
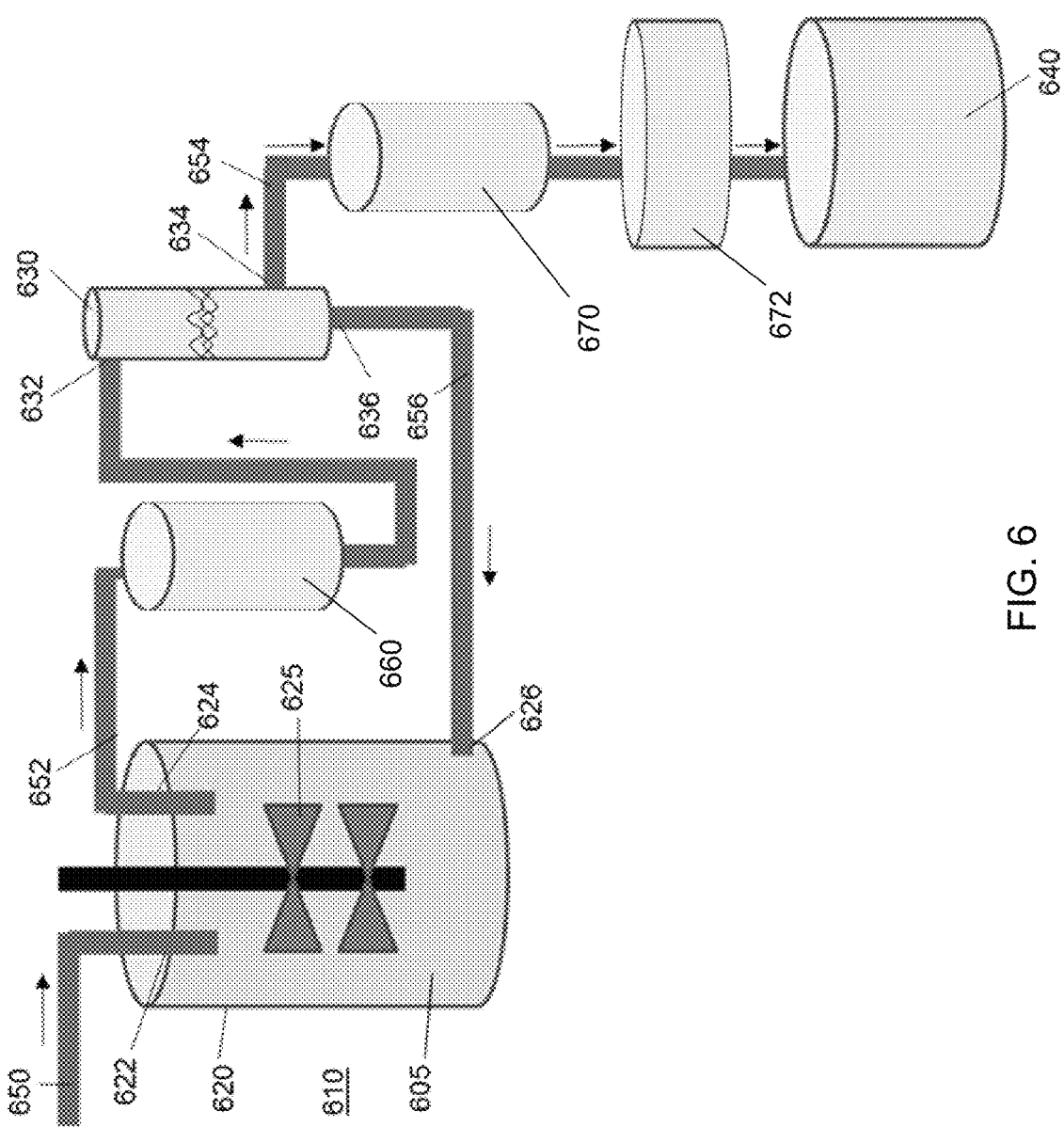
FIG. 6 is a schematic view illustrating a system of the present disclosure, including a perfusion bioreactor with an acoustophoretic separation device and filtrations stages/steps located upstream and downstream of the acoustophoretic separation device, and a recycle path.

FIG. 6 illustrates an exemplary processing system of the present disclosure, comprising a bioreactor 610 and a filtering device 630. The system is set up for use as a perfusion bioreactor. The bioreactor 610 includes a reaction vessel 620 having a feed inlet 622, an outlet 624, and a recycle inlet 626. Media is added into the feed inlet 622 by an addition pipe 650. The contents of the reaction vessel (reference numeral 605) are mixed with an agitator 625. The desired product (e.g. recombinant proteins, viruses, exosomes, or additional cells) is continuously produced by the cells located within the vessel 620, and are present in the media of the bioreactor. The product and the cells in the perfusion bioreactor are drawn from the reaction vessel through pipe 652, and enter the acoustophoretic filtering device 630 through inlet 632. There, the desired product is separated from the cells through the use of multi-dimensional standing waves. The desired product can be drawn off through a product outlet 634 and pipe 654 into a containment vessel 640. The cells are returned to the perfusion bioreactor after separation, passing from recycle outlet 636 of the filtering device through pipe 656 to recycle inlet 626 of the reaction vessel, which form a recycle path. The 3-D standing waves of the acoustophoresis device allow for high throughput of the perfusion reactor due to the increased lateral trapping force of the 3-D standing waves. It is noted that although the reaction vessel outlet 624 is depicted at the top of the vessel and the recycle inlet 626 is depicted at the bottom of the vessel, that this arrangement can be reversed if desired. This may depend on the desired product to be obtained.

Figure 19:
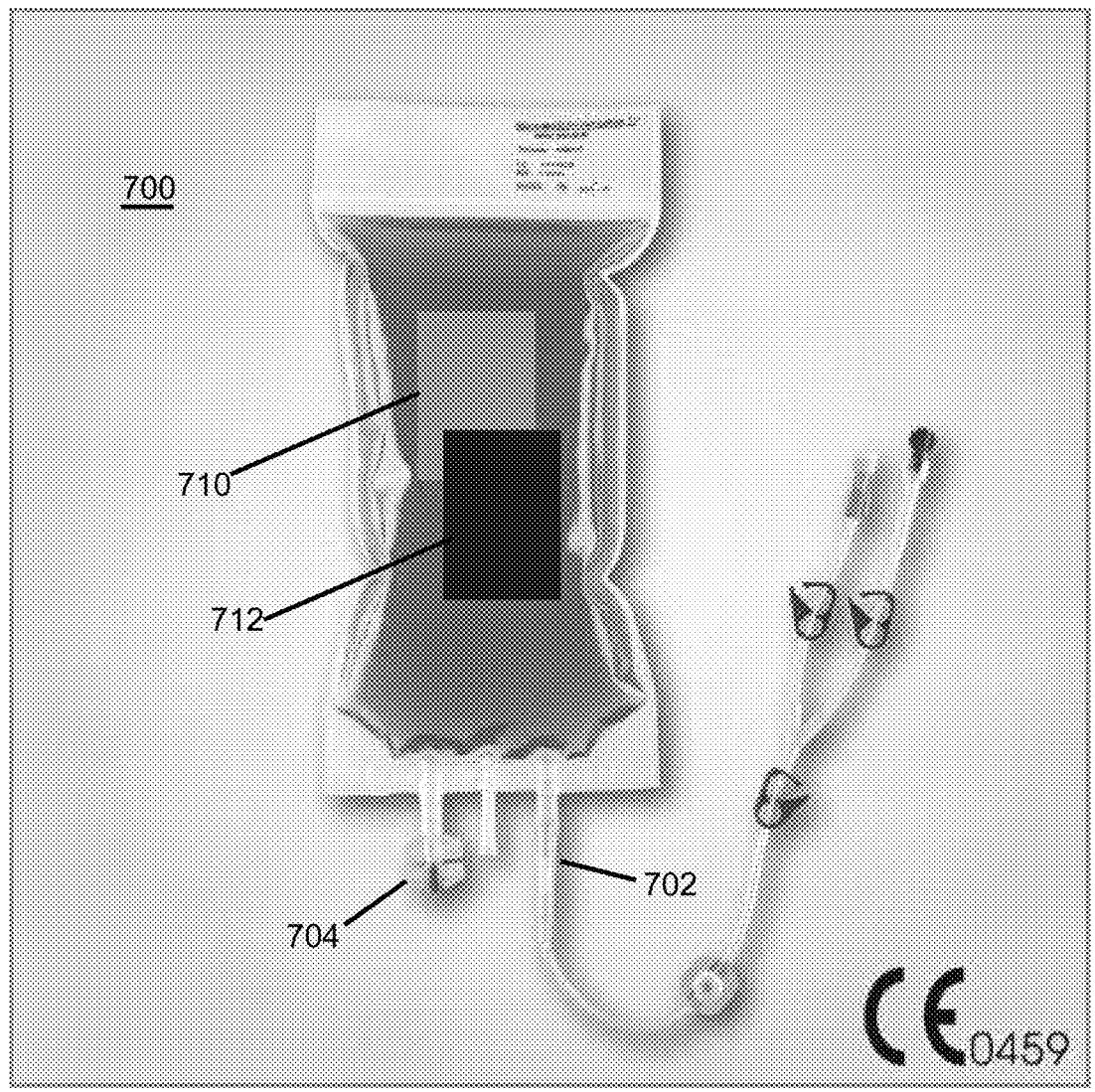
FIG. 19 is an illustration of an embodiment where the filtering device is in the form of a flexible bag.

In additional embodiments, it is particularly contemplated that the filtering device 630 is in the form of a flexible bag or pouch. Such a filtering device is illustrated in FIG. 19. The interior volume of the flexible bag 700 operates as the flow chamber. The flexible bag includes an inlet 702 and an outlet 704. Opposite surfaces of the flexible bag can be stiff. One surface includes an ultrasonic transducer 710, and the opposite surface includes a reflector 712 opposite the transducer, so that a multi-dimensional acoustic standing wave can be generated within the bag.

Figure 7:
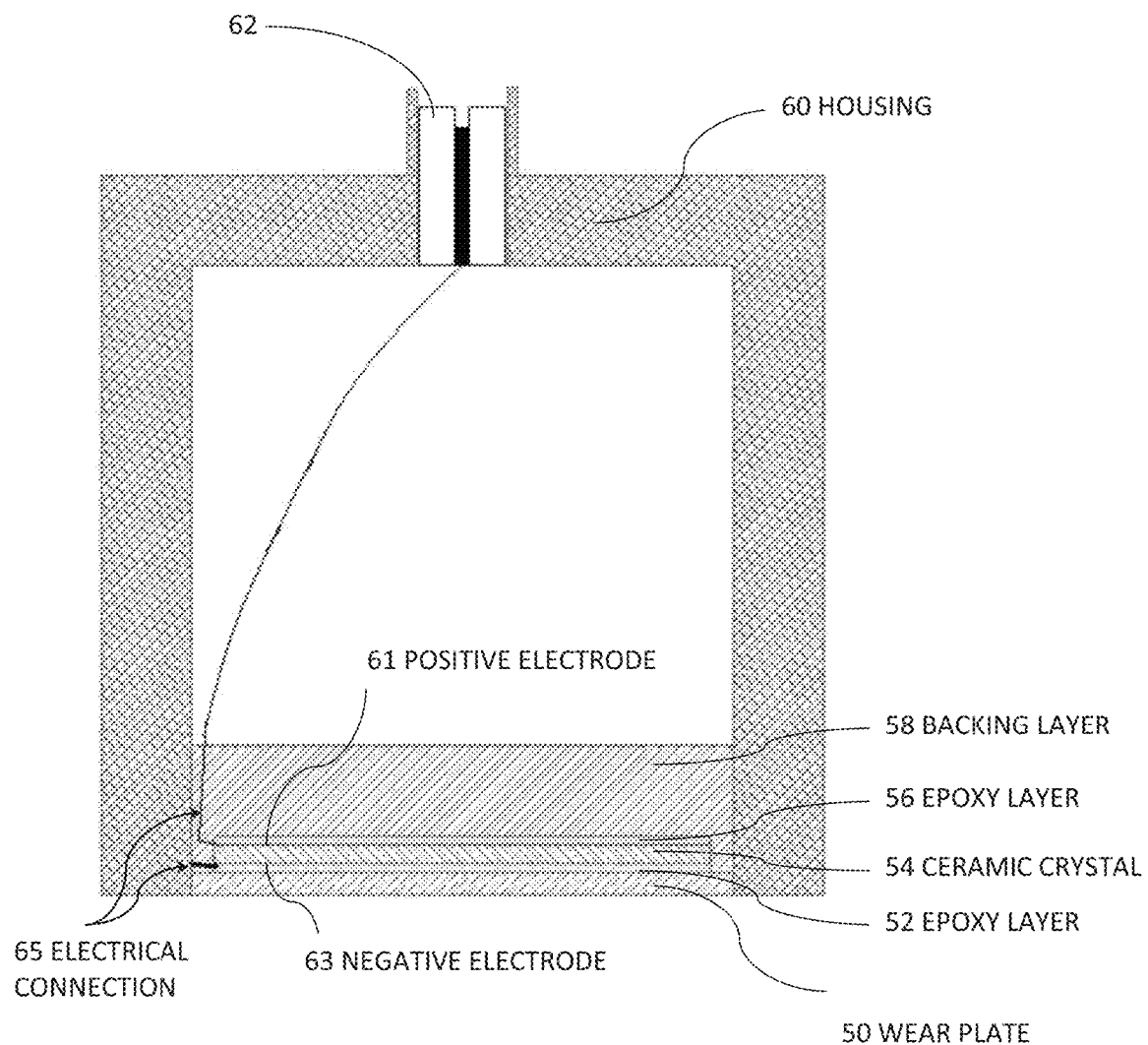
FIG. 7 is a cross-sectional diagram of a conventional ultrasonic transducer.

Referring to both FIG. 6 and FIG. 7, cell culture media and cells are drawn from the reaction vessel through pipe 652, and enter the flexible bag 700 through inlet 702. The multi-dimensional acoustic standing wave traps the desired product (i.e. cells). The cell culture media and other material exit through the outlet 704 through pipe 656 back to recycle inlet 626 of the reaction vessel. Eventually, as the bag fills up with concentrated cells, the fluid flow through the bag 700 is stopped. The bag filled with concentrated cells can then be taken out of the recycle path between the product outlet 634 and the recycle inlet 626 of the reaction vessel. The concentrated cells are then recovered from the bag.

In other embodiments, it is particularly contemplated that a flexible bag or pouch is used within the flow chamber of the filtering device 630 for the capture of cells. This flexible bag or pouch is similar to the bag 700 of FIG. 19, but does not have the ultrasonic transducer and reflector attached thereto. Cell culture media and cells are drawn from the reaction vessel through pipe 652, and enter the acoustophoretic filtering device 630 through inlet 632. The flexible bag itself contains an inlet and an outlet, and the acoustophoretic filtering device acts as a housing for the bag. The multi-dimensional acoustic standing wave traps the desired product (i.e. cells). The cell culture media and other material exit through the outlet of the bag and out through recycle outlet 636 of the filtering device through pipe 656 to recycle inlet 626 of the reaction vessel, which form a recycle path.

Within the flexible bag, as the quantity of trapped cells increases, the cells form larger clusters that will fall out of the acoustic standing wave at a critical size due to gravity forces. The clusters fall to the bottom of the bag. Eventually, as the bag fills up with concentrated cells, the fluid flow through the filtering device 630 is stopped. The bag filled with concentrated cells can then be removed and a new bag placed within the filtering device 630. Referring to FIG. 6, the filtering device inlet 632 would probably be near the middle of the filtering device 630, and the recycle outlet 636 would probably be located at the top of the filtering device, with the concentrated cells falling to the bottom of the flexible bag to be collected. No product outlet 634 or containment vessel 640 would be needed to collect the product, which would be collected in the flexible bag that is subsequently removed from the flow chamber of the filtering device 630.

It may be helpful now to describe the ultrasonic transducer(s) used in the acoustophoretic filtering device in more detail. FIG. 7 is a cross-sectional diagram of a conventional ultrasonic transducer. This transducer has a wear plate 50 at a bottom end, epoxy layer 52, ceramic crystal 54 (made of, e.g. Lead Zirconate Titanate (PZT)), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figure 8:
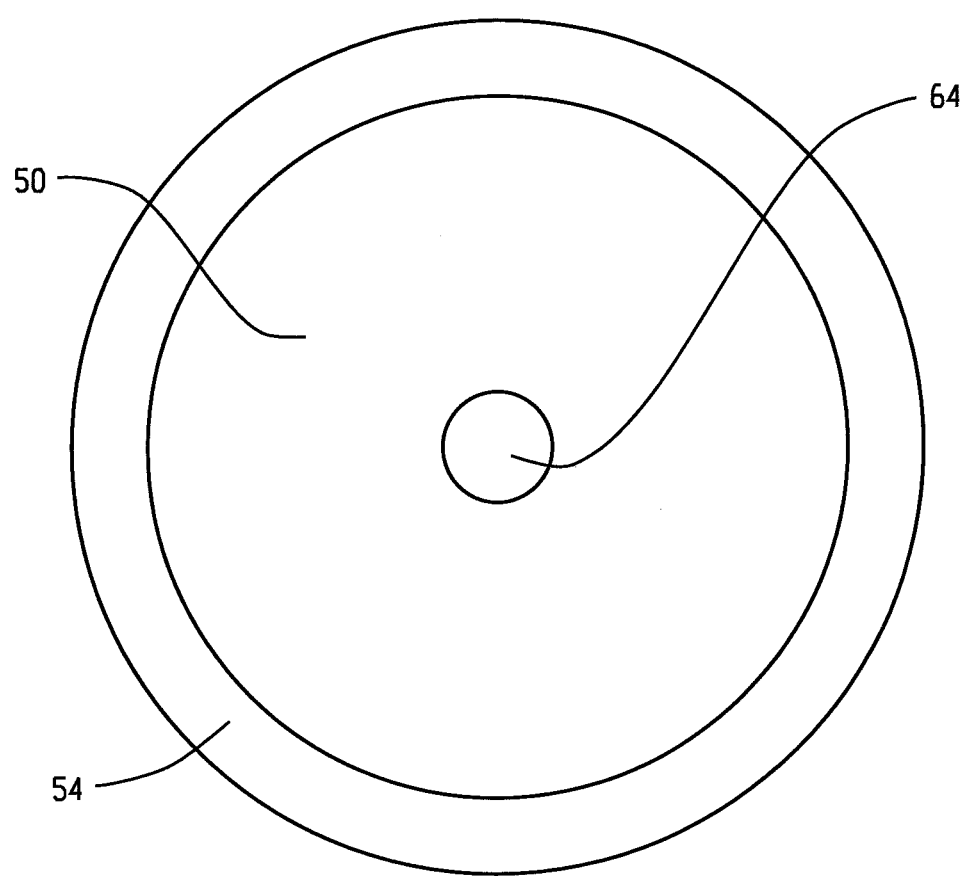
FIG. 8 is a picture of a wear plate of a conventional transducer.

FIG. 8 is a photo of a wear plate 50 with a bubble 64 where the wear plate has pulled away from the ceramic crystal surface due to the oscillating pressure and heating.

Figure 9:
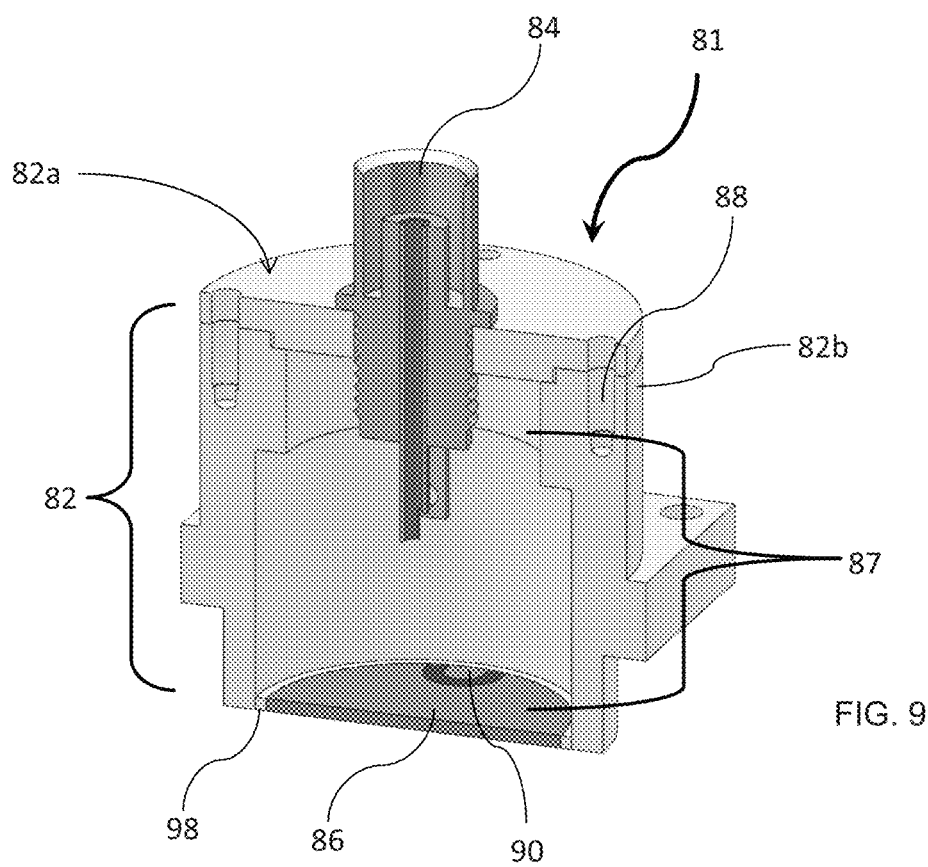
FIG. 9 is a cross-sectional diagram of an ultrasonic transducer of the present disclosure. An air gap is present within the transducer, and no backing layer or wear plate is present.

FIG. 9 is a cross-sectional view of an ultrasonic transducer 81 of the present disclosure, which is used in the acoustophoretic filtering devices of the present disclosure. Transducer 81 has an aluminum housing 82. A PZT crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present.

Figure 10:
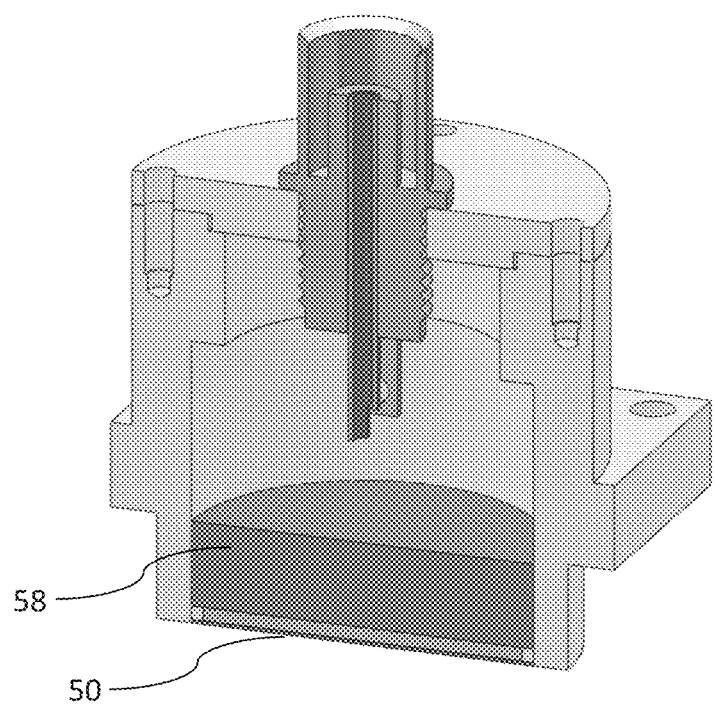
FIG. 10 is a cross-sectional diagram of an ultrasonic transducer of the present disclosure. An air gap is present within the transducer, and a backing layer and wear plate are present.

Screws (not shown) attach an aluminum top plate 82a of the housing to the body 82b of the housing via threads 88. The top plate includes a connector 84 to pass power to the PZT crystal 86. The bottom and top surfaces of the PZT crystal 86 are each connected to an electrode (positive and negative), such as silver or nickel. A wrap-around electrode tab 90 connects to the bottom electrode and is isolated from the top electrode. Electrical power is provided to the PZT crystal 86 through the electrodes on the crystal, with the wrap-around tab 90 being the ground connection point. Note that the crystal 86 has no backing layer or epoxy layer as is present in FIG. 5. Put another way, there is an air gap 87 in the transducer between aluminum top plate 82a and the crystal 86 (i.e. the air gap is completely empty). A minimal backing 58 and/or wear plate 50 may be provided in some embodiments, as seen in FIG. 10.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes with a high Q-factor. The vibrating ceramic crystal/disk is directly exposed to the fluid flowing through the flow chamber.

Removing the backing (e.g. making the crystal air backed) also permits the ceramic crystal to vibrate at higher order modes of vibration with little damping (e.g. higher order modal displacement). In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines.

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymer. Organic and biocompatible coatings such as silicone or polyurethane are also usable as a wear surface.

In some embodiments, the ultrasonic transducer has a 1 inch diameter and a nominal 2 MHz resonance frequency. Each transducer can consume about 28 W of power for droplet trapping at a flow rate of 3 GPM. This power usage translates to an energy cost of 0.25 kW hr/m$^3$. This measure is an indication of the very low cost of energy of this technology. Desirably, each transducer is powered and controlled by its own amplifier. In other embodiments, the ultrasonic transducer uses a square crystal, for example with 1"×1" dimensions. Alternatively, the ultrasonic transducer can use a rectangular crystal, for example with 1"×2.5" dimensions. Power dissipation per transducer was 10 W per 1"×1" transducer cross-sectional area and per inch of acoustic standing wave span in order to get sufficient acoustic trapping forces. For a 4" span of an intermediate scale system, each 1"×1" square transducer consumes 40 W. The larger 1"×2.5" rectangular transducer uses 100 W in an intermediate scale system. The array of three 1"×1" square transducers would consume a total of 120 W and the array of two 1"×2.5" transducers would consume about 200 W. Arrays of closely spaced transducers represent alternate potential embodiments of the technology. Transducer size, shape, number, and location can be varied as desired to generate desired three-dimensional acoustic standing wave patterns.

The size, shape, and thickness of the transducer determine the transducer displacement at different frequencies of excitation, which in turn affects separation efficiency. Typically, the transducer is operated at frequencies near the thickness resonance frequency (half wavelength). Gradients in transducer displacement typically result in more trapping locations for the cells/biomolecules. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

To investigate the effect of the transducer displacement profile on acoustic trapping force and separation efficiencies, an experiment was repeated ten times using a 1"×1" square transducer, with all conditions identical except for the excitation frequency. Ten consecutive acoustic resonance frequencies, indicated by circled numbers 1-9 and letter A on FIG. 11, were used as excitation frequencies. The conditions were experiment duration of 30 min, a 1000 ppm oil concentration of approximately 5-micron SAE-30 oil droplets, a flow rate of 500 ml/min, and an applied power of 20 W. Oil droplets were used because oil is denser than water, and can be separated from water using acoustophoresis.

Figure 11:
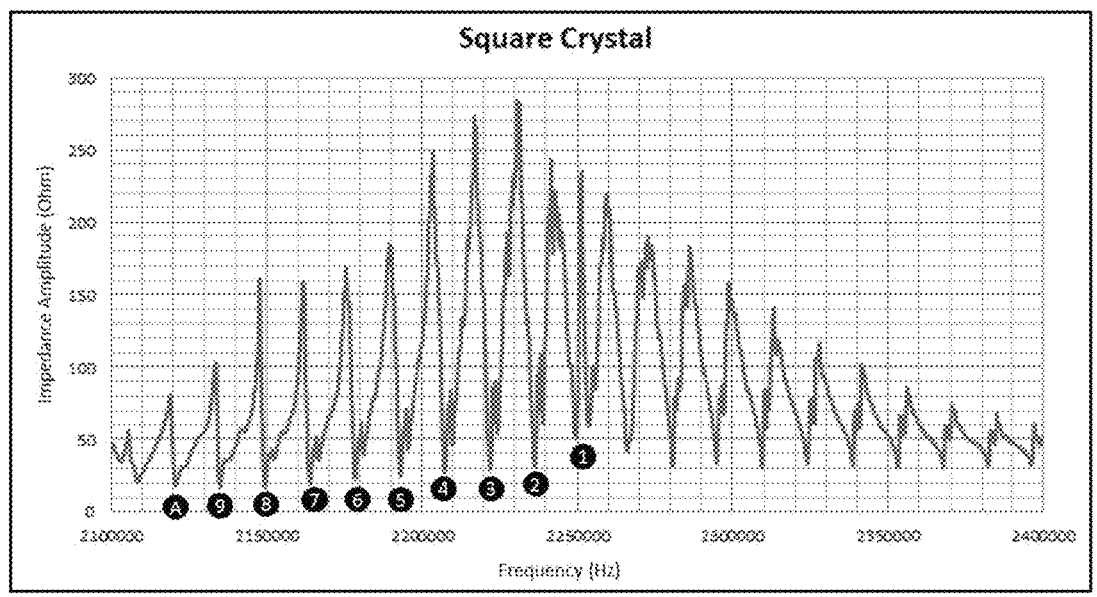
FIG. 11 is a graph of electrical impedance amplitude versus frequency for a square transducer driven at different frequencies.

FIG. 11 shows the measured electrical impedance amplitude of a square transducer as a function of frequency in the vicinity of the 2.2 MHz transducer resonance. The minima in the transducer electrical impedance correspond to acoustic resonances of the water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. As an example, at one frequency of excitation with a single line of trapped oil droplets, the displacement has a single maximum in the middle of the electrode and minima near the transducer edges. At another excitation frequency, the transducer profile has multiple maxima leading to multiple trapped lines of oil droplets. Higher order transducer displacement patterns result in higher trapping forces and multiple stable trapping lines for the captured oil droplets.

Figure 12:
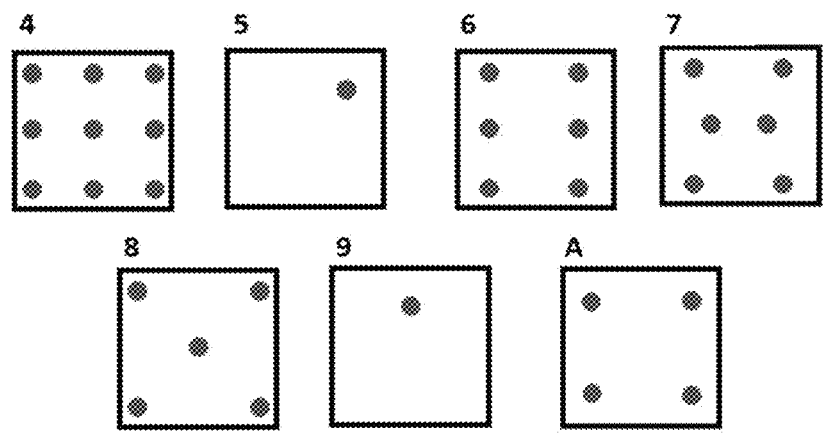
FIG. 12 illustrates the trapping line configurations for seven of the peak amplitudes of FIG. 11 from the direction orthogonal to fluid flow.

As the oil-water emulsion passed by the transducer, the trapping lines of oil droplets were observed and characterized. The characterization involved the observation and pattern of the number of trapping lines across the fluid channel, as shown in FIG. 12, for seven of the ten resonance frequencies identified in FIG. 11. Different displacement profiles of the transducer can produce different (more) trapping lines in the standing waves, with more gradients in displacement profile generally creating higher trapping forces and more trapping lines.

Figure 13:
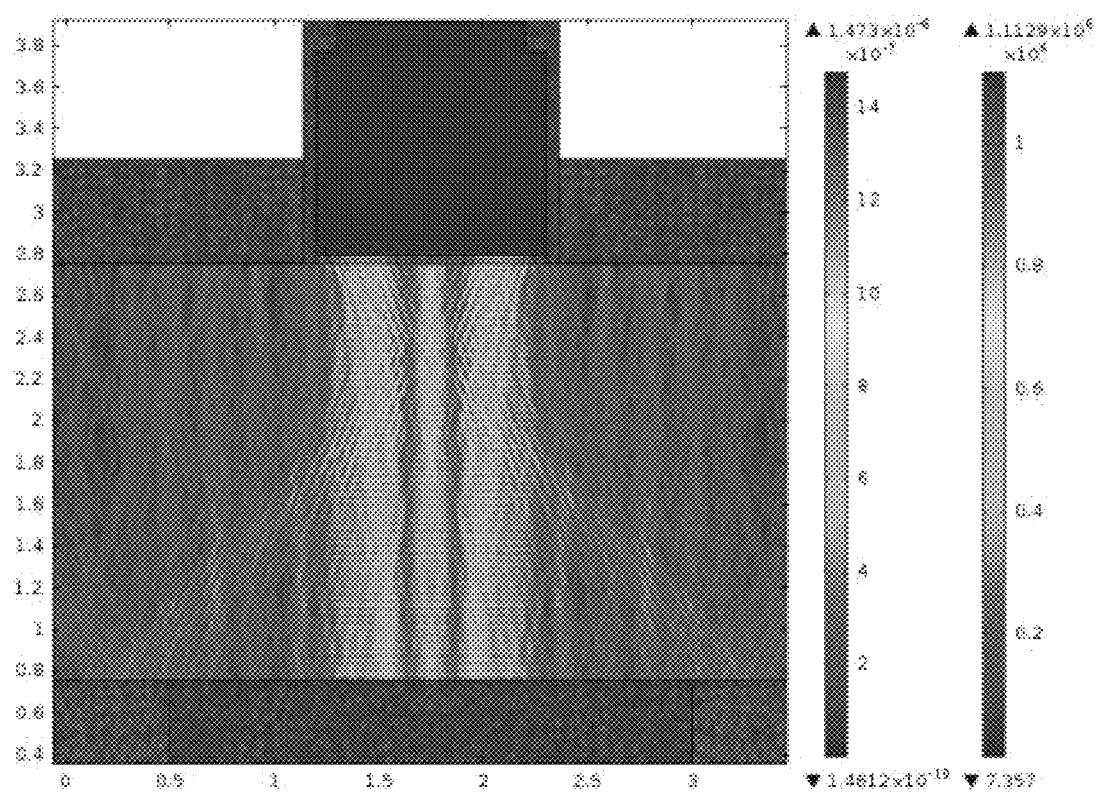
FIG. 13 is a computer simulation of the acoustic pressure amplitude (right-hand scale in Pa) and transducer out of plane displacement (left-hand scale in meters). The text at the top of the left-hand scale reads "×10$^{-7}$". The text at the top of the left-hand scale by the upward-pointing triangle reads "1.473×10$^{-6}$". The text at the bottom of the left-hand scale by the downward-pointing triangle reads "1.4612×10$^{-10}$". The text at the top of the right-hand scale reads "×10$^{6}$". The text at the top of the right-hand scale by the upward-pointing triangle reads "1.1129×10$^{6}$". The text at the bottom of the right-hand scale by the downward-pointing triangle reads "7.357". The triangles show the maximum and minimum values depicted in this figure for the given scale. The horizontal axis is the location within the chamber along the X-axis, in inches, and the vertical axis is the location within the chamber along the Y-axis, in inches.

FIG. 13 is a numerical model showing a pressure field that matches the 9 trapping line pattern. The numerical model is a two-dimensional model; and therefore only three trapping lines are observed. Two more sets of three trapping lines exist in the third dimension perpendicular to the plane of the page.

In the present system examples, the system is operated at a voltage such that the particles (i.e. biomolecules or cells) are trapped in the ultrasonic standing wave, i.e., remain in a stationary position. The particles are collected in along well defined trapping lines, separated by half a wavelength. Within each nodal plane, the particles are trapped in the minima of the acoustic radiation potential. The axial component of the acoustic radiation force drives particles with a positive contrast factor to the pressure nodal planes, whereas particles with a negative contrast factor are driven to the pressure anti-nodal planes. The radial or lateral component of the acoustic radiation force is the force that traps the particle. It therefore, for particle trapping, is larger than the combined effect of fluid drag force and gravitational force. In systems using typical transducers, the radial or lateral component of the acoustic radiation force is typically several orders of magnitude smaller than the axial component of the acoustic radiation force. However, the lateral force generated by the transducers of the present disclosure can be significant, on the same order of magnitude as the axial force component, and is sufficient to overcome the fluid drag force at linear velocities of up to 1 cm/s.

The lateral force can be increased by driving the transducer in higher order mode shapes, as opposed to a form of vibration where the crystal effectively moves as a piston having a uniform displacement. The acoustic pressure is proportional to the driving voltage of the transducer. The electrical power is proportional to the square of the voltage. The transducer is typically a thin piezoelectric plate, with electric field in the z-axis and primary displacement in the z-axis. The transducer is typically coupled on one side by air (i.e. the air gap within the transducer) and on the other side by the fluid of the cell culture media. The types of waves generated in the plate are known as composite waves. A subset of composite waves in the piezoelectric plate is similar to leaky symmetric (also referred to as compressional or extensional) Lamb waves. The piezoelectric nature of the plate typically results in the excitation of symmetric Lamb waves. The waves are leaky because they radiate into the water layer, which result in the generation of the acoustic standing waves in the water layer. Lamb waves exist in thin plates of infinite extent with stress free conditions on its surfaces. Because the transducers of this embodiment are finite in nature, the actual modal displacements are more complicated.

Figure 14:
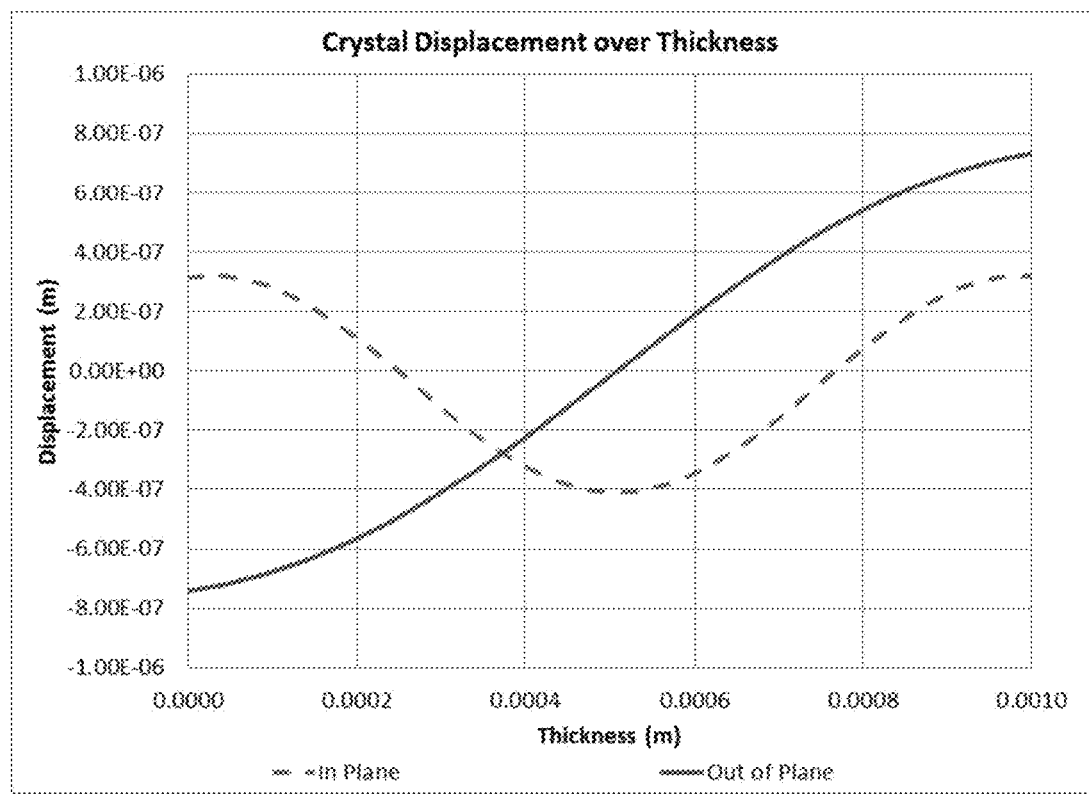
FIG. 14 shows the In-Plane and Out-of-Plane displacement of a crystal where composite waves are present.

FIG. 14 shows the typical variation of the in-plane displacement (x-displacement) and out-of-plane displacement (y-displacement) across the thickness of the plate, the in-plane displacement being an even function across the thickness of the plate and the out-of-plane displacement being an odd function. Because of the finite size of the plate, the displacement components vary across the width and length of the plate. In general, a (m,n) mode is a displacement mode of the transducer in which there are m undulations in transducer displacement in the width direction and n undulations in the length direction, and with the thickness variation as described in FIG. 14. The maximum number of m and n is a function of the dimension of the crystal and the frequency of excitation.

The transducers are driven so that the piezoelectric crystal vibrates in higher order modes of the general formula (m, n), where m and n are independently 1 or greater. Generally, the transducers will vibrate in higher order modes than (2,2). Higher order modes will produce more nodes and antinodes, result in three-dimensional standing waves in the fluid layer, characterized by strong gradients in the acoustic field in all directions, not only in the direction of the standing waves, but also in the lateral directions. As a consequence, the acoustic gradients result in stronger trapping forces in the lateral direction.

In embodiments, the pulsed voltage signal driving the transducer can have a sinusoidal, square, sawtooth, or triangle waveform; and have a frequency of 500 kHz to 10 MHz. The pulsed voltage signal can be driven with pulse width modulation, which produces any desired waveform. The pulsed voltage signal can also have amplitude or frequency modulation start/stop capability to eliminate streaming.

The transducer(s) is/are used to create a pressure field that generates forces of the same order of magnitude both orthogonal to the standing wave direction and in the standing wave direction. When the forces are roughly the same order of magnitude, particles of size 0.1 microns to 300 microns will be moved more effectively towards regions of agglomeration ("trapping lines"). Because of the equally large gradients in the orthogonal acoustophoretic force component, there are "hot spots" or particle collection regions that are not located in the regular locations in the standing wave direction between the transducer and the reflector. Hot spots are located in the maxima or minima of acoustic radiation potential. Such hot spots represent particle collection locations which allow for better wave transmission between the transducer and the reflector during collection and stronger inter-particle forces, leading to faster and better particle agglomeration.

Figure 15:
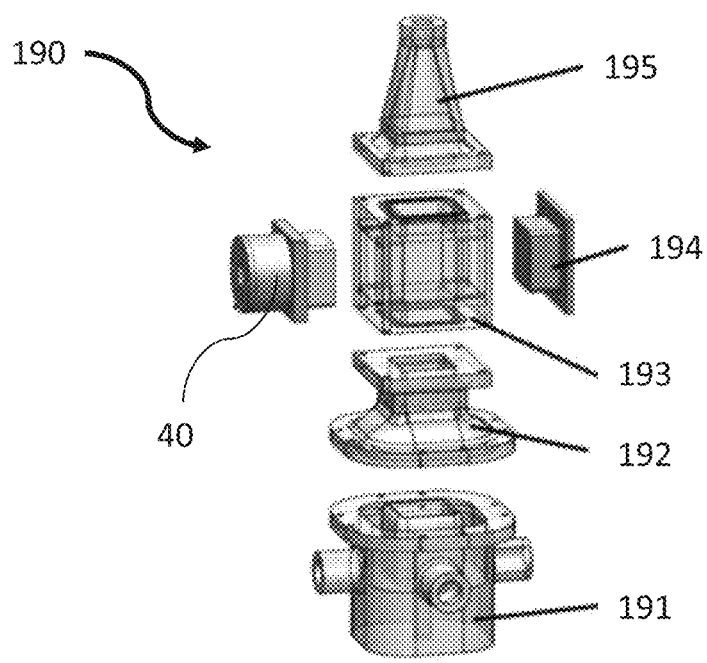
FIG. 15 shows an exploded view of an acoustophoretic separator used for conducting some example separations, having one flow chamber.
Figure 16:
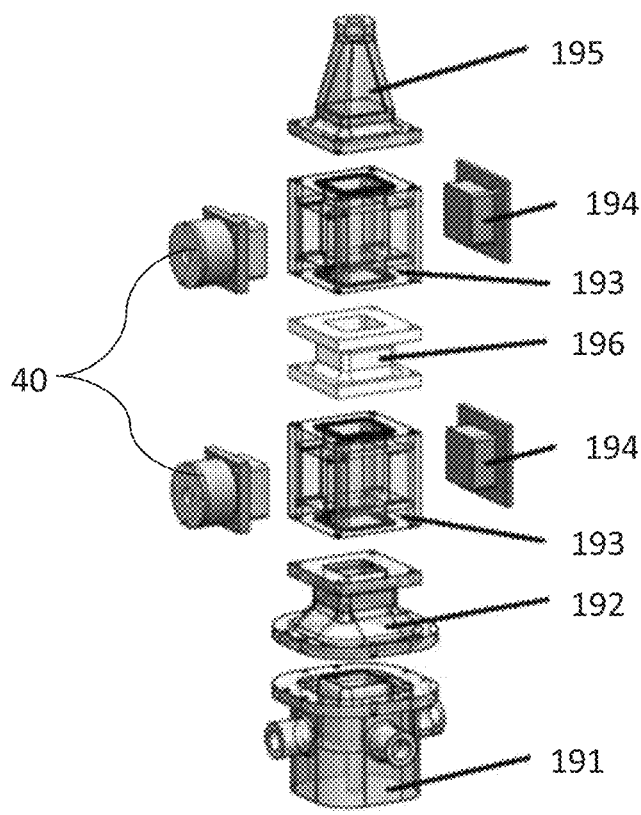
FIG. 16 shows an exploded view of a stacked acoustophoretic separator with two flow chambers.

FIG. 15 and FIG. 16 are exploded views showing the various parts of acoustophoretic separators. FIG. 15 has only one separation chamber, while FIG. 16 has two separation chambers.

Referring to FIG. 15, fluid enters the separator 190 through a four-port inlet 191. A transition piece 192 is provided to create plug flow through the separation chamber 193. A transducer 40 and a reflector 194 are located on opposite walls of the separation chamber. Fluid then exits the separation chamber 193 and the separator through outlet 195.

FIG. 16 has two separation chambers 193. A system coupler 196 is placed between the two chambers 193 to join them together.

Acoustophoretic separation has been tested on different lines of Chinese hamster ovary (CHO) cells. In one experiment, a solution with a starting cell density of $8.09 \times 10^6$ cells/mL, a turbidity of 1,232 NTU, and cell viability of roughly 75% was separated using a system as depicted in FIG. 15. The transducers were 2 MHz crystals, run at approximately 2.23 MHz, drawing 24-28 Watts. A flow rate of 25 mL/min was used. The result of this experiment is shown in FIG. 17.

In another experiment, a solution with a starting cell density of $8.09 \times 10^6$ cells/mL, a turbidity of 1,232 NTU, and cell viability of roughly 75% was separated. This CHO cell line had a bi-modal particle size distribution (at size 12 μm and 20 μm). The result is shown in FIG. 18.

Figure 17:
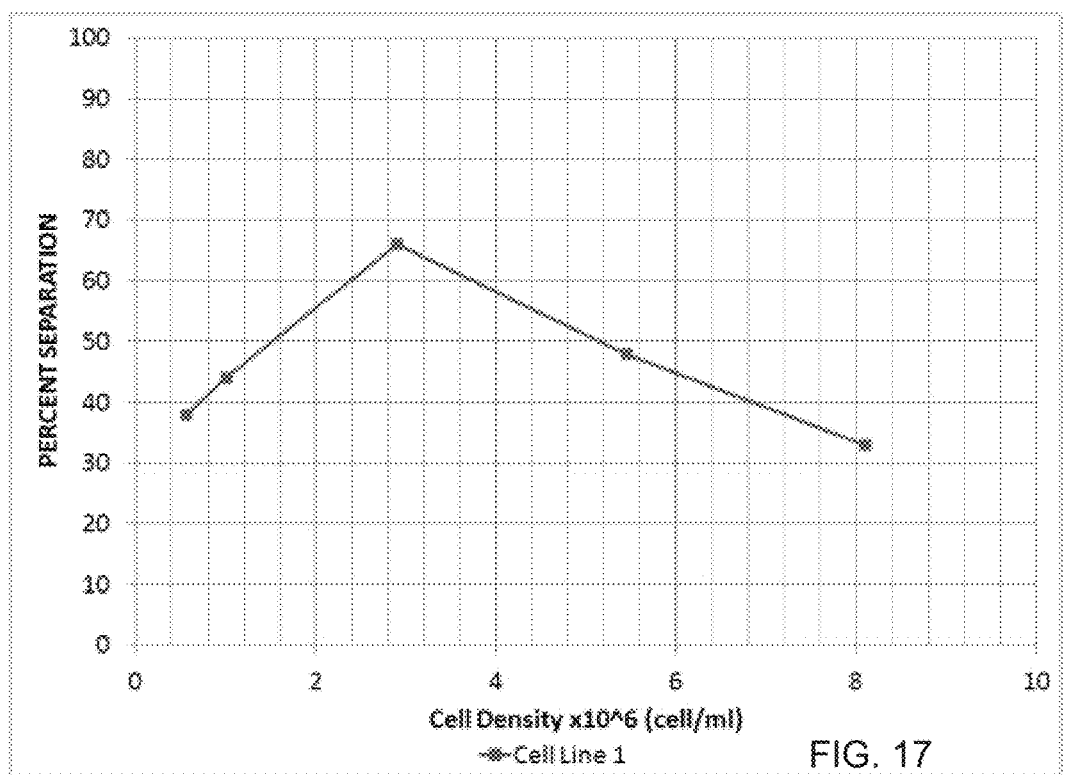
FIG. 17 is a graph showing the efficiency of removing cells from a medium using a Beckman Coulter Cell Viability Analyzer for one experiment.
Figure 18:
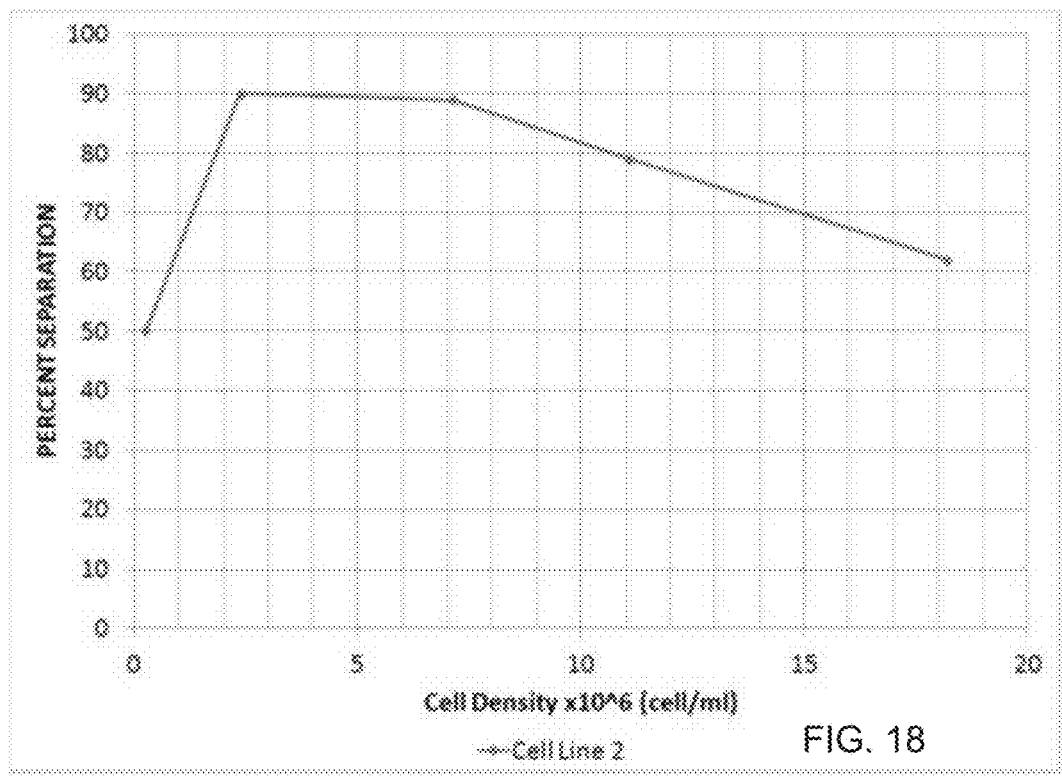
FIG. 18 is a graph showing the efficiency of removing cells from a medium using a Beckman Coulter Cell Viability Analyzer for another experiment.

FIG. 17 and FIG. 18 were produced by a Beckman Coulter Cell Viability Analyzer. Other tests revealed that frequencies of 1 MHz and 3 MHz were not as efficient as 2 MHz at separating the cells from the fluid.

In other tests at a flow rate of 10 L/hr, 99% of cells were captured with a confirmed cell viability of more than 99%. Other tests at a flow rate of 50 mL/min (i.e. 3 L/hr) obtained a final cell density of $3 \times 10^6$ cells/mL with a viability of nearly 100% and little to no temperature rise. In yet other tests, a 95% reduction in turbidity was obtained at a flow rate of 6 L/hr.

Further testing was performed using yeast as a simulant for CHO for the biological applications. For these tests, at a flow rate of 15 L/hr, various frequencies were tested as well as power levels. Table 1 shows the results of the testing.

TABLE 1

2.5" × 4" System results at 15 L/hr Flow rate

| Frequency (MHz) | 30 Watts | 37 Watts | 45 Watts |
| --- | --- | --- | --- |
| 2.2211 | 93.9 | 81.4 | 84.0 |
| 2.2283 | 85.5 | 78.7 | 85.4 |
| 2.2356 | 89.1 | 85.8 | 81.0 |
| 2.243 | 86.7 | — | 79.6 |

In biological applications, it is contemplated that all of the parts of the system (e.g. the flow chamber, tubing leading to and from the bioreactor or filtering device, the sleeve containing the ultrasonic transducer and the reflector, the temperature-regulating jacket, etc.) can be separated from each other and be disposable. Avoiding centrifuges and filters allows better separation of the CHO cells without lowering the viability of the cells. The transducers may also be driven to create rapid pressure changes to prevent or clear blockages due to agglomeration of CHO cells. The frequency of the transducers may also be varied to obtain optimal effectiveness for a given power.

It is contemplated that the acoustophoretic separators/filtering devices of the present disclosure can be used in a filter "train," in which multiple different filtration steps are used to clarify or purify an initial fluid/particle mixture to obtain the desired product and manage different materials from each filtration step. Each filtration step can be optimized to remove a particular material, improving the overall efficiency of the clarification process. An individual acoustophoretic device can operate as one or multiple filtration steps. For example, each individual ultrasonic transducer within a particular acoustophoretic device can be operated to trap materials within a given particle range. It is particularly contemplated that the acoustophoretic device can be used to remove large quantities of material, reducing the burden on subsequent downstream filtration steps/stages. However, it is contemplated that additional filtration steps/stages can be placed upstream or downstream of the acoustophoretic device, such as physical filters or other filtration mechanisms known in the art, such as depth filters (e.g., polymeric morphology, matrix media adsorption), sterile filters, cross-flow filters (e.g., hollow fiber filter cartridges), tangential flow filtration cassettes, adsorption columns, separation columns (e.g., chromatography columns), or centrifuges. Multiple acoustophoretic devices can be used as well. It is particularly contemplated that desirable biomolecules or cells can be recovered/separated after such filtration/purification, as explained herein.

The outlets of the acoustophoretic separators/filtering devices of the present disclosure (e.g., product outlet, recycle outlet) can be fluidly connected to any other filtration step or filtration stage. Similarly, the inlets of the acoustophoretic separators/filtering devices of the present disclosure could also be fluidly connected to any other filtration step or filtration stage. That is, it is specifically contemplated that the additional filtration steps/stages could be located either upstream (i.e., between the acoustophoretic separators(s) and the bioreactor), downstream, or both upstream and downstream of the acoustophoretic separators(s). In particular, it is to be understood that the acoustophoretic separators of the present disclosure can be used in a system with as few or as many filtration stages/steps located upstream or downstream thereof as is desired. For avoidance of doubt, it is contemplated that the present systems can include a bioreactor, an acoustophoretic separator/filtering device, and multiple filtrations stages/steps located upstream and downstream of the acoustophoretic separator, with the filtrations stage(s) and acoustophoretic separator(s) generally serially arranged and fluidly connected to one another. For example, FIG. 6 schematically illustrates such a system, including a bioreactor 610, an acoustophoretic filtering device 630, an upstream filtration stage 660, a downstream porous filter stage 670, and a downstream separation column filtration stage 672. These filtering stages 630, 660, 670, 672 are arranged in series.

For example, when it is desired that the system include a filtration stage (e.g., a porous filter) located upstream of the acoustophoretic separator, the outlet of the bioreactor can lead to an inlet of the porous filter and the outlet of the porous filter can lead to an inlet of the acoustophoretic separator, with the porous filter pre-processing the fluid therein. As another example, when it is desired that the system include a filtration stage (e.g., a separation column) located downstream of the acoustophoretic separator, the outlet of the bioreactor can lead to an inlet of the acoustophoretic separator and the outlet of the acoustophoretic separator can lead to an inlet of the separation column, with the separation column further processing the fluid therein.

It is specifically contemplated that such filtration steps/stages can include various methods such as an additional acoustophoretic separator/filtering device, or physical filtration means known in the art, such as depth filtration, sterile filtration, size exclusion filtration, or tangential filtration. Depth filtration uses physical porous filtration mediums that can retain material through the entire depth of the filter. In sterile filtration, membrane filters with extremely small pore sizes are used to remove microorganisms and viruses, generally without heat or irradiation or exposure to chemicals. Size exclusion filtration separates materials by size and/or molecular weight using physical filters with pores of given size. In tangential filtration, the majority of fluid flow is across the surface of the filter, rather than into the filter.

Chromatography can also be used, including cationic chromatography columns, anionic chromatography columns, affinity chromatography columns, mixed bed chromatography columns. Other hydrophilic/hydrophobic processes can also be used for filtration purposes.

The present disclosure has been described with reference to exemplary embodiments. Modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A system comprising:
   a bioreactor;
   an acoustophoretic separator downstream of and fluidly connected to the bioreactor, comprising:
   a flow chamber; and
   an ultrasonic transducer and a reflector located opposite the ultrasonic transducer so as to produce a multi-dimensional standing wave in the flow chamber; and
   a downstream filtration stage downstream of and fluidly connected to the acoustophoretic separator.

2. The system of claim 1, wherein the downstream filtration stage is selected from the group consisting of depth filters, sterile filters, and crossflow filters.

3. The system of claim 1, wherein the downstream filtration stage isolates the desired product by size exclusion filtration.

4. The system of claim 1, wherein the downstream filtration stage includes a plurality of filtration stages arranged in series.

5. The system of claim 4, wherein at least one of the plurality of filtration stages is a separation column and another of the plurality of filtration stages is a porous filter, the porous filter located upstream of the separation column and fluidly connected thereto.

6. The system of claim 1, wherein the multi-dimensional standing wave has an axial force component and a lateral force component which are of the same order of magnitude.

7. The system of claim 1, wherein the downstream filtration stage is a second acoustophoretic separator comprising an ultrasonic transducer-reflector pair driven to produce a multi-dimensional standing wave in the second acoustophoretic separator that is adapted to trap desired product that is not trapped in the first acoustophoretic separator.

8. The system of claim 1, wherein the bioreactor is a perfusion bioreactor.

9. A process of isolating and recovering a desired product from a cell culture media, comprising:
   sending the cell culture media from a bioreactor to an acoustophoretic separator, wherein the acoustophoretic separator comprises:
   a flow chamber; and
   an ultrasonic transducer and a reflector located opposite the ultrasonic transducer;
   producing a multi-dimensional standing wave in the flow chamber to separate the desired product from the cell culture media;
   passing a concentrated flow of the desired product from the acoustophoretic separator to a downstream filtration stage;
   recovering the desired product from the downstream filtration stage.

10. The process of claim 9, further comprising sending the cell culture media from the flow chamber back to the bioreactor through a recycle outlet of the acoustophoretic separator.

11. A system comprising:
    a bioreactor;
    an upstream filtration stage fluidly connected to the bioreactor and upstream of an acoustophoretic separator; and
    the acoustophoretic separator fluidly connected to and downstream of the upstream filtration stage, the acoustophoretic separator comprising:
    a flow chamber; and
    an ultrasonic transducer and a reflector located opposite the ultrasonic transducer so as to produce a multi-dimensional standing wave in the flow chamber;
    a recycle outlet downstream of the flow chamber connected to a recycle inlet of the reaction vessel, for sending the associated fluid containing cells back to the bioreactor.

12. The system of claim 11, wherein the upstream filtration stage is selected from the group consisting of depth filters, sterile filters, and crossflow filters.

13. The system of claim 11, wherein the upstream filtration stage isolates the desired product by size exclusion filtration.

14. The system of claim 11, wherein the upstream filtration stage includes a plurality of filtration stages arranged in series.

15. The system of claim 14, wherein at least one of the plurality of filtration stages is a separation column and another of the plurality of filtration stages is a porous filter, the porous filter located upstream of the separation column and fluidly connected thereto.

16. The system of claim 11, wherein the multi-dimensional standing wave has an axial force component and a lateral force component which are of the same order of magnitude.

17. The system of claim 11, wherein the upstream filtration stage is a second acoustophoretic separator comprising an ultrasonic transducer-reflector pair driven to produce a second multi-dimensional standing wave in the second acoustophoretic separator.

18. The system of claim 11, wherein the bioreactor is a perfusion bioreactor.

19. The system of claim 17, wherein the second multi-dimensional standing wave has an axial force component and a lateral force component which are of the same order of magnitude.

* * * * *